US 7,828,437 B2

(12) United States Patent
Kikawa et al.

(10) Patent No.: US 7,828,437 B2
(45) Date of Patent: Nov. 9, 2010

(54) FUNDUS OCULI OBSERVATION DEVICE AND FUNDUS OCULI IMAGE PROCESSING DEVICE

(75) Inventors: Tsutomu Kikawa, Tokyo (JP); Takashi Fujimura, Tokyo (JP); Hiroyuki Aoki, Tokyo (JP); Jun Suehiro, Tokyo (JP); Yasufumi Fukuma, Fort Lee, NJ (US)

(73) Assignee: Kabushi Kaisha Topcon, Tokyo (JP)

( * ) Notice: Subject to any disclaimer, the term of this patent is extended or adjusted under 35 U.S.C. 154(b) by 327 days.

(21) Appl. No.: 12/035,879

(22) Filed: Feb. 22, 2008

(65) Prior Publication Data

US 2008/0204655 A1 Aug. 28, 2008

(30) Foreign Application Priority Data

Feb. 26, 2007 (JP) .............................. 2007-045831

(51) Int. Cl.
*A61B 3/14* (2006.01)
(52) U.S. Cl. ....................................... 351/206; 351/200
(58) Field of Classification Search .................. 351/206
See application file for complete search history.

(56) References Cited

U.S. PATENT DOCUMENTS

2007/0002277 A1* 1/2007 Hanebuchi ................... 351/206

FOREIGN PATENT DOCUMENTS

| EP | 1652469 | 5/2006 |
|----|---------|--------|
| EP | 1775545 | 4/2007 |
| EP | 1836952 | 9/2007 |
| JP | 2003-000543 | 1/2003 |
| JP | 2004-502483 | 1/2004 |
| JP | 2004-052195 | 2/2004 |
| JP | 2004-350849 | 12/2004 |
| WO | WO-2004/098396 | 11/2004 |
| WO | WO-2007/016397 | 2/2007 |

OTHER PUBLICATIONS

M. Shimazawa et al., "Morphometric evaluation of changes with time in optic disc structure and thickness of retinal nerve fibre layer in chronic ocular hypertensive monkeys," Experimental Eye Research, vol. 82, 2006, pp. 427-440.
V. E. Malinovsky, "An overview of the Heidelberg Retina Tomograph," Journal of the American Optometric Association, vol. 67, No. 8, Aug. 1996, pp. 457-467.
European Search Report mailed Jul. 15, 2008, issued on the corresponding European application No. 08003295.6.

* cited by examiner

*Primary Examiner*—Jordan M. Schwartz
*Assistant Examiner*—James C Jones
(74) *Attorney, Agent, or Firm*—Edwards Angell Palmer & Dodge LLP

(57) ABSTRACT

A fundus oculi observation device comprises: an image forming part configured to optically acquire data and form a tomographic image of a fundus oculi of an eye; a storage configured to store optical information representing a state of an ocular optical system of the eye; a calculator configured to calculate a magnification of the ocular optical system, based on the optical information; and an analyzer configured to analyze the tomographic image, based on the magnification.

13 Claims, 16 Drawing Sheets

FUNDUS OCULI OBSERVATION DEVICE AND FUNDUS OCULI IMAGE PROCESSING DEVICE

BACKGROUND OF THE INVENTION

1. Field of the Invention

The present invention relates to a fundus oculi observation device for observing a fundus oculi, and a fundus oculi image processing device for processing a fundus oculi image.

2. Description of the Related Art

As a fundus oculi observation device, a retinal camera has been widely used conventionally. FIG. 15 shows an example of the appearance of a general retinal camera used conventionally. FIG. 16 shows an example of the configuration of an optical system internally accommodated in the retinal camera (refer to Japanese Unexamined Patent Application Publication No. 2004-350849, for example). Herein, "observation" includes at least a case of observing a photographed fundus oculi image (observation of a fundus oculi with a naked eye may be included).

First, referring to FIG. 15, the appearance of a conventional retinal camera 1000 will be described. This retinal camera 1000 is provided with a platform 3 mounted on a base 2 so as to be slidable in the front and rear, right and left directions (horizontal directions). On this platform 3, an operation panel 3a and a control lever 4 for an examiner to perform various operations are mounted.

The examiner can freely move the platform 3 on the base 2 by operating the control lever 4. On the top of the control lever 4, an operation button 4a pressed down for requiring execution of production of a fundus oculi image is mounted.

On the base 2, a post 5 is mounted standing upward. This post 5 is provided with a jaw rest 6 where a jaw of a subject is rested, and an external fixation lamp 7 serving as a light source for fixing an eye E.

On the platform 3, a main body part 8 is placed for accommodating various optical systems and control systems of the retinal camera 1000. The control system may be placed, for example, inside the base 2 or the platform 3, or in an external device such as a computer connected to the retinal camera 1000.

On the side of the eye E of the main body part 8, an objective lens part 8a placed facing the eye E is disposed. On the examiner's side, an eyepiece part 8b is disposed.

Further, to the main body part 8, a still camera 9 for producing a still image of the fundus oculi of the eye E and an imaging device 10 such as a TV camera for producing a still image or moving image of the fundus oculi are connected. The still camera 9 and the imaging device 10 are formed so as to be removable from the main body part 8.

As the still camera 9, in accordance with various conditions such as the purpose of an examination and a method of saving a photographed image, a digital camera equipped with a CCD, a film camera, an instant camera and the like may be interchangeably used as necessary. The main body part 8 is provided with a mounting part 8c for interchangeably mounting the still camera 9.

In a case where the still camera 9 and the imaging device 10 are of digital imaging type, it is possible to transmit and store image data into an image recording device such as a computer connected to the retinal camera 1000.

Furthermore, on the examiner's side of the main body part 8, a touch panel monitor 11 is disposed. On this touch panel monitor 11, a fundus oculi image of the eye E formed based on video signals outputted from the (digital-type) still camera 9 or imaging device 10 is displayed. Moreover, on the touch panel monitor 11, an x-y coordinate system taking the center of a screen as the origin is displayed superimposed on the fundus oculi image. When the examiner touches the screen, coordinate values corresponding to a touched position are displayed.

Next, referring to FIG. 16, the configuration of the optical system of the retinal camera 1000 will be described. The retinal camera 1000 is provided with an illumination optical system 100 that illuminates a fundus oculi Ef of the eye E, and an imaging optical system 120 that guides the illumination light reflected by the fundus oculi to the eyepiece part 8b, the still camera 9 and the imaging device 10.

The illumination optical system 100 comprises: a halogen lamp 101; a condenser lens 102; a xenon lamp 103; a condenser lens 104; exciter filters 105 and 106; a ring transparent plate 107; a mirror 108; an LCD 109; an illumination diaphragm 110; a relay lens 111; an aperture mirror 112; and an objective lens 113.

The halogen lamp 101 is an observation light source that emits continuous light. The condenser lens 102 is an optical element for converging the continuous light (observation illumination light) emitted by the halogen lamp 101 and evenly applying the observation illumination light to the eye E (fundus oculi Ef).

The xenon lamp 103 is an imaging light source that is flashed at the time of imaging of the fundus oculi Ef. The condenser lens 104 is an optical element for converging the flash light (imaging illumination light) emitted by the xenon lamp 103 and evenly applying the imaging illumination light to the fundus oculi Ef.

The exciter filters 105 and 106 are filters used at the time of fluorography of an image of the fundus oculi Ef. The exciter filters 105 and 106 can be respectively inserted into and removed from an optical path by a drive mechanism such as a solenoid. The exciter filter 105 is placed on the optical path at the time of FAG (fluorescein angiography). The exciter filter 106 is placed on the optical path at the time of ICG (indocyanine green angiography). At the time of color-imaging, both the exciter filters 105 and 106 are retracted from the optical path.

The ring transparent plate 107 is placed in a conjugating position with a pupil of the eye E, and is provided with a ring transparent part 107a taking the optical axis of the illumination optical system 100 as the center. The mirror 108 reflects the illumination light emitted by the halogen lamp 101 or xenon lamp 103, in a direction of the optical axis of the imaging optical system 120. The LCD 109 displays a fixation target (not illustrated) for fixing the eye E.

The illumination diaphragm 110 is a diaphragm member to shut out part of the illumination light in order to prevent flare and the like. This illumination diaphragm 110 is configured so as to be movable in the optical axis direction of the illumination optical system 100, and is thus capable of changing an illumination region of the fundus oculi Ef.

The aperture mirror 112 is an optical element that combines the optical axis of the illumination optical system 100 and the optical axis of the imaging optical system 120. In the center region of the aperture mirror 112, an aperture 112a is opened. The optical axis of the illumination optical system 100 and the optical axis of the imaging optical system 120 cross each other at a substantially central position of the aperture 112a. The objective lens 113 is installed in the objective lens part 8a of the main body part 8.

The illumination optical system 100 having such a configuration illuminates the fundus oculi Ef in the following manner. First, at the time of fundus oculi observation, the halogen lamp 101 is turned on and an observation illumination light is emitted. This observation illumination light is applied to the ring transparent plate 107 through the condenser lenses 102 and 104. The light passed through the ring transparent part 107a of the ring transparent plate 107 is reflected by the mirror 108 and, after passing through the LCD 109, the illumination diaphragm 110 and the relay lens 111, is reflected by the aperture mirror 112 so as to be along the optical axis direction of the imaging optical system 120. Then, the light is converged by the objective lens 113 to enter the eye E, thereby illuminating the fundus oculi Ef.

At this moment, since the ring transparent plate 107 is placed in a conjugating position with the pupil of the eye E, a ring-shaped image of the observation illumination light entering the eye E is formed on the pupil. The entering fundus oculi reflection light of the entered observation illumination light is emitted from the eye E through a central dark part of the ring-shaped image on the pupil.

On the other hand, at the time of imaging of the fundus oculi Ef, flush light is emitted from the xenon lamp 103, and the imaging illumination light is applied to the fundus oculi Ef through the same path. In the case of fluorography, either the exciter filter 105 or the exciter filter 106 is selectively placed on the optical path, depending on whether FAG imaging or ICG imaging is carried out.

The imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a quick return mirror 127; and an imaging media 9a. Herein, the imaging media 9a is an imaging media (a CCD, camera film, instant film or the like) for the still camera 9.

The fundus oculi reflection light of the illumination light exiting through the central dark part of the ring-shaped image formed on the pupil of the eye E enters the imaging diaphragm 121 through the aperture 112a of the aperture mirror 112. The aperture mirror 112 reflects cornea reflection light of the illumination light, and acts so as not to mix the cornea reflection light into the fundus oculi reflection light entering the imaging diaphragm 121. Consequently, generation of flare in observation images and photographed images is inhibited.

The imaging diaphragm 121 is a plate-shaped member having a plurality of circular light-transmitting parts of different sizes. The plurality of light-transmitting parts compose diaphragms with different diaphragm values (F values), and are placed alternatively on the optical path by a drive mechanism (not illustrated).

The barrier filters 122 and 123 can be inserted into and removed from the optical path by a drive mechanism such as a solenoid. In FAG imaging, the barrier filter 122 is placed on the optical path, whereas in ICG imaging, the barrier filter 123 is placed on the optical path. Further, at the time of color-imaging, both the barrier filters 122 and 123 are retracted from the optical path.

The variable magnifying lens 124 is movable in the optical axis direction of the imaging optical system 120 by a drive mechanism (not illustrated). This makes it possible to change an observation magnification and an imaging magnification, and to focus images of the fundus oculi. The imaging lens 126 is a lens that focuses the fundus oculi reflection light from the eye E onto the imaging media 9a.

The quick return mirror 127 is disposed so as to be capable of being rotated around a rotary shaft 127a by a drive mechanism (not illustrated). In a case where imaging of the fundus oculi Ef is performed with the still camera 9, the fundus oculi reflection light is guided to the imaging media 9a by springing up the quick return mirror 127 that is obliquely mounted on the optical path. Meanwhile, in a case where imaging of the fundus oculi is performed with the imaging device 10, or in a case where observation of the fundus oculi is performed with the naked eye of the examiner, the quick return mirror 127 is obliquely mounted on the optical path to upwardly reflect the fundus oculi reflection light.

The imaging optical system 120 is further provided with, for guiding the fundus oculi reflection light reflected by the quick return mirror 127, a field lens 128, a switching mirror 129, an eyepiece 130, a relay lens 131, a reflection mirror 132, an imaging lens 133, and an image pick-up element 10a. The image pick-up element 10a is an image pick-up element such as a CCD installed in the imaging device 10. On the touch panel monitor 11, a fundus oculi image Ef' imaged by the image pick-up element 10a is displayed.

The switching mirror 129 is rotatable around a rotary shaft 129a in the same manner as the quick return mirror 127. This switching mirror 129 is obliquely disposed on the optical path during observation with the naked eye, thereby reflecting and guiding the fundus oculi reflection light to the eyepiece 130.

In the case of imaging of a fundus oculi image by the imaging device 10, the switching mirror 129 is retracted from the optical path. The fundus oculi reflection light is focused on the image pick-up element 10a via the relay lens 131, the mirror 132 and the imaging lens 133, and the fundus oculi image Ef' is displayed on the touch panel monitor 11.

The retinal camera 1000 is a fundus oculi observation device used for observing the surface of the fundus oculi Ef, namely, the surface of the retina. On the other hand, layers such as a photoreceptor layer and a retinal pigment epithelium layer are present in a deep part of the retina, and moreover, organs such as choroidea and sclera are present in a deeper part. Recently, a device for observing these deep tissues has been practically implemented (refer to Japanese Unexamined Patent Application Publications Nos. JP-A 2003-000543, JP-A 2005-241464 and JP-A 2004-502483).

Each of the fundus oculi observation devices disclosed in JP-A 2003-000543, JP-A 2005-241464 and JP-A 2004-502483 is a device to which a so-called OCT (Optical Coherence Tomography) technology is applied (referred to as an optical image measurement device, an optical coherence tomography device, and the like). Such a fundus oculi observation device is a device that splits low-coherence light into two, guides one (signal light) of the lights to the fundus oculi and the other (reference light) to a given reference object and, based on interference light obtained by superimposing the signal light passed through the fundus oculi and the reference light reflected by the reference object, forms tomographic images of the surface and deep layer tissue of the fundus oculi.

The fundus oculi observation device disclosed in JP-A 2004-502483 has a function of presenting the thickness of a layer of the fundus oculi in a quadrant. The thickness of a layer of the fundus oculi is regarded as important information in diagnosis of glaucoma and the like.

For evaluation of the thickness of a layer of the fundus oculi, it is carried out in common to measure the thickness of the layer by setting circular measurement lines on the fundus oculi as shown in FIG. 17 and analyzing tomographic images along the respective measurement lines. Circular measurement lines M1, M2 and M3 have radii of m1, m2 and m3, respectively. The radii m1, m2 and m3 are set to, for example, 1.2 mm, 1.6 mm and 2.0 mm, respectively. The measurement lines M1, M2 and M3 are set concentrically, and a center C thereof is set to the center position of the optic papilla.

In this evaluation of the thickness of a layer of the fundus oculi, a measurement error resulting from the ocular optical system of an eye may occur. Influences of the ocular optical system on a light applied to the fundus oculi are different depending on eyes, but in the conventional way, the measurement lines M1, M2 and M3 are set regardless of the differences among individuals. Therefore, it has been difficult to set the positions of the radii m1, m2 and m3 from the center C of the optic papilla at proper positions, namely, accurately set.

In the conventional way, the measurement lines M1, M2 and M3 are set as described below. First, the refractive power and axial length of the ocular optical system of an eye are measured in advance. Next, the corneal curvature of the eye is estimated by using the result of the measurement and the refractive power of the lens of the Gullstrand's eye model. Subsequently, the magnification of the ocular optical system is calculated by using the estimated value and so on. Then, the radii m1, m2 and m3 are determined by using the value of the magnification, and the measurement lines M1, M2 and M3 are set.

However, since this method employs a standard value based on the eye model, it has been difficult to accurately obtain the magnification of the eye. Therefore, it has been difficult to set the measurement lines M1, M2 and M3 at proper positions with respect to the eye.

An influence of the magnification of the ocular optical system exists at all times when the position and distance on the fundus oculi are considered, not only when the thickness of the layer of the fundus oculi is evaluated.

SUMMARY OF THE INVENTION

The present invention has been made to solve these problems, and an object of the present invention is to provide a fundus oculi observation device and fundus oculi image processing device in which the magnification of the ocular optical system of an eye can be accurately obtained.

In order to achieve the aforementioned object, in a first aspect of the present invention, a fundus oculi observation device comprises: an image forming part configured to optically acquire data and form a tomographic image of a fundus oculi of an eye; a storage configured to store optical information representing a state of an ocular optical system of the eye; a calculator configured to calculate a magnification of the ocular optical system, based on the optical information; and an analyzer configured to analyze the tomographic image, based on the magnification.

In a second aspect of the present invention, a fundus oculi image processing device comprises: a storage configured to store tomographic images of a fundus oculi of an eye and optical information indicating a state of an ocular optical system of the eye; a calculator configured to calculate a magnification of the ocular optical system, based on the optical information; and an analyzer configured to analyze the tomographic images, based on the magnification.

DESCRIPTION OF THE DRAWINGS

FIG. 8A shows an example of the feature of scan with a signal light when a fundus oculi is seen from the incident side of the signal light with respect to an eye. FIG. 8B shows an example of the feature of arrangement of scanning points on each scanning line.

DETAILED DESCRIPTION OF THE PREFERRED EMBODIMENT

Figure 1:
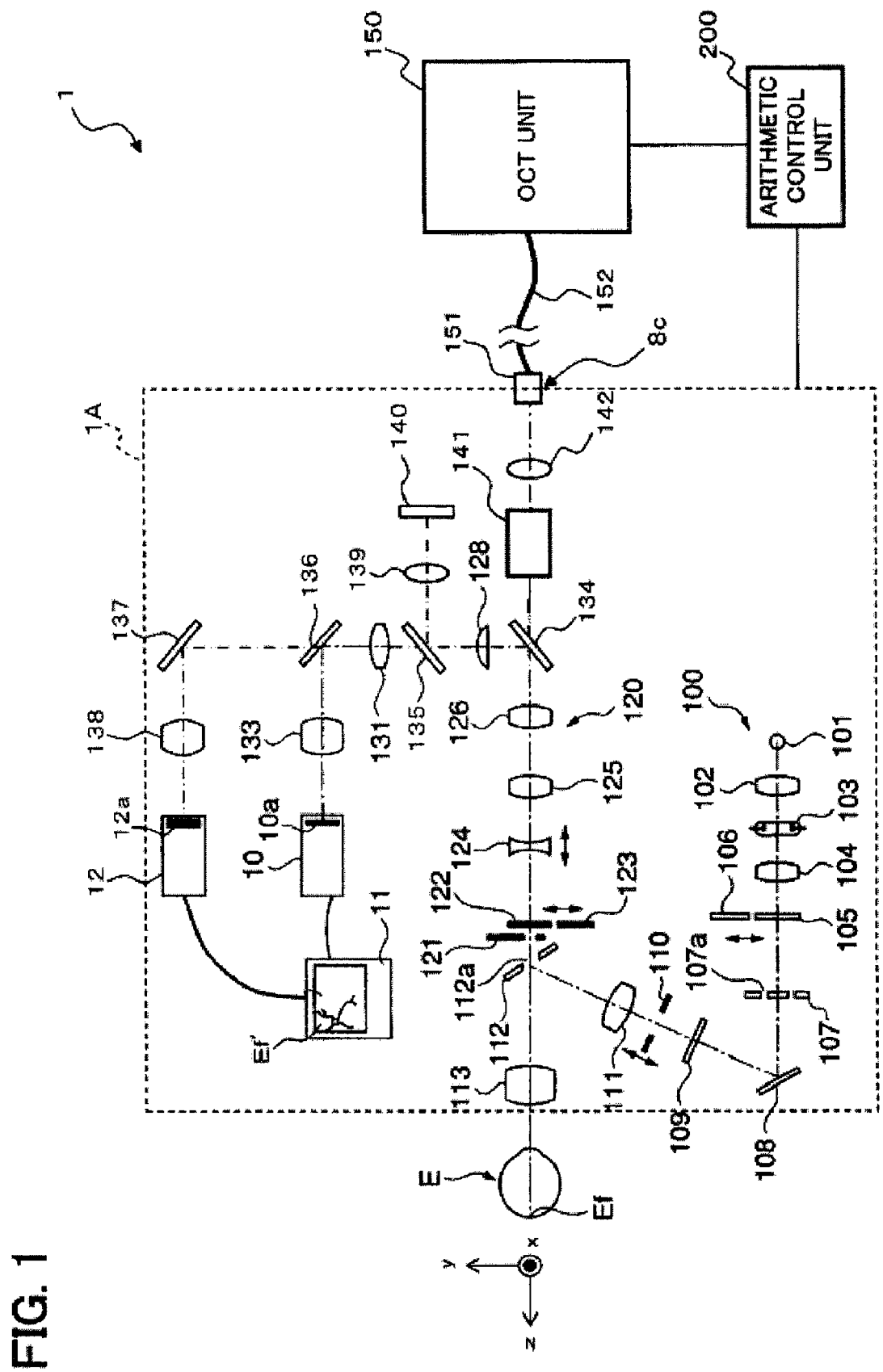
FIG. 1 is a schematic configuration diagram showing an example of the entire configuration in a preferred embodiment of the fundus oculi observation device according to the present invention.

An example of a preferred embodiment of a fundus oculi observation device and a fundus oculi image processing device according to the present invention will be described in detail referring to the drawings. Herein, the same components as the conventional ones shown in FIGS. 15 and 16 will be denoted by the same reference numerals used therein.

[Configuration of Device]

Figure 2:
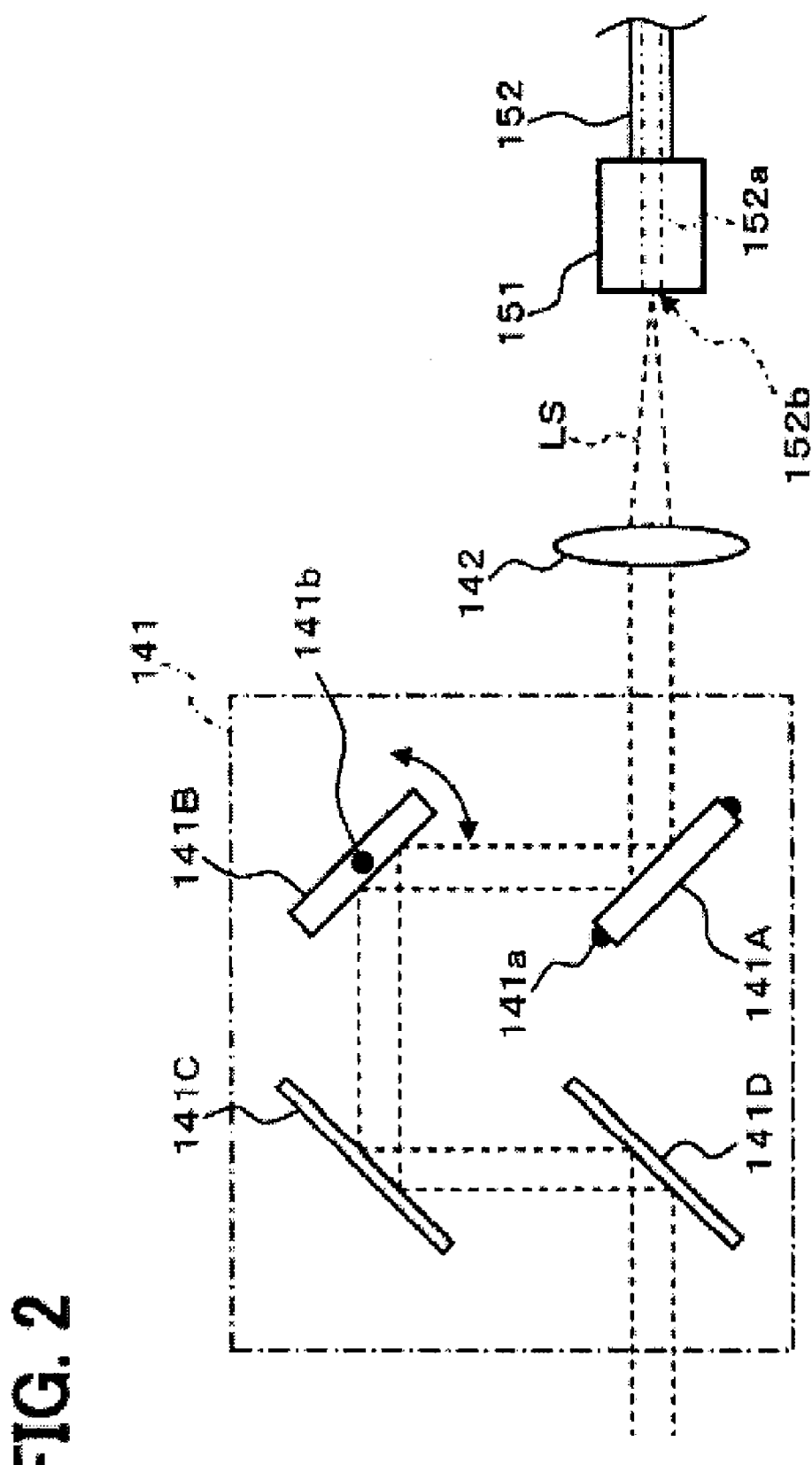
FIG. 2 is a schematic configuration diagram showing an example of the configuration of a scanning unit installed in a retinal camera unit in the preferred embodiment of the fundus oculi observation device according to the present invention.
Figure 3:
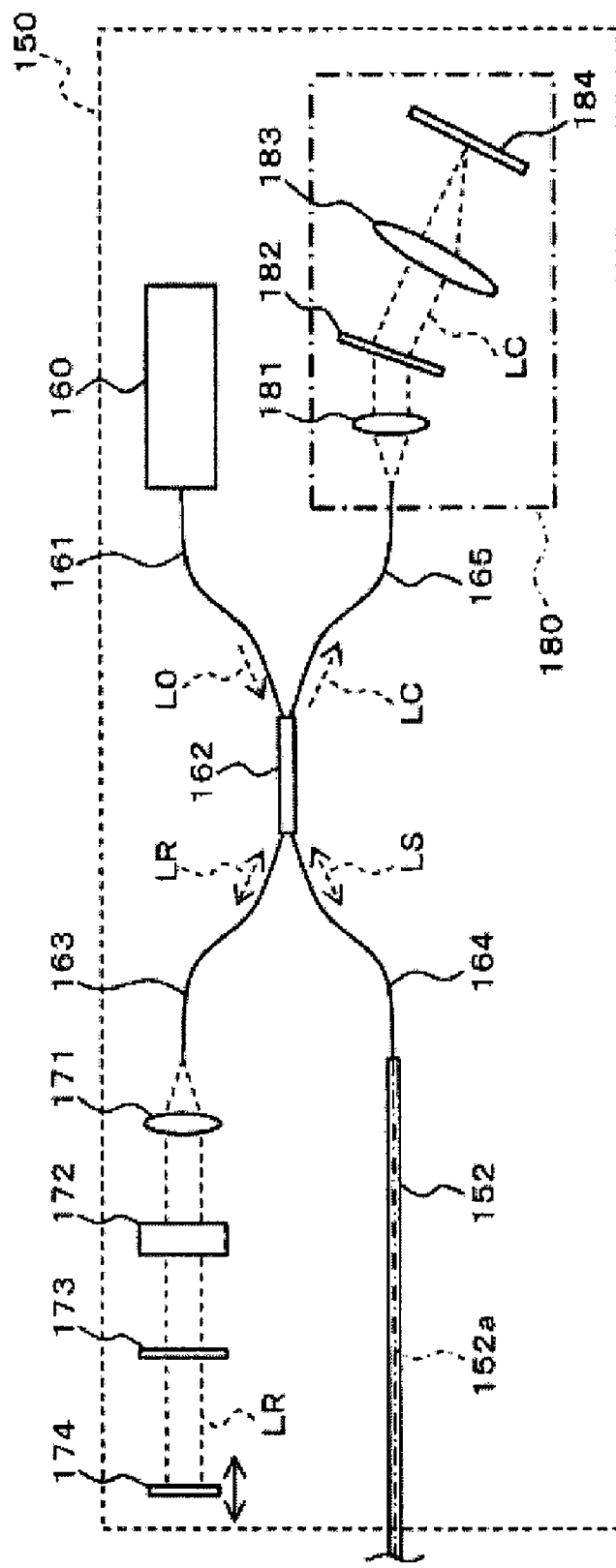
FIG. 3 is a schematic configuration diagram showing an example of the configuration of an OCT unit in the preferred embodiment of the fundus oculi observation device according to the present invention.
Figure 4:
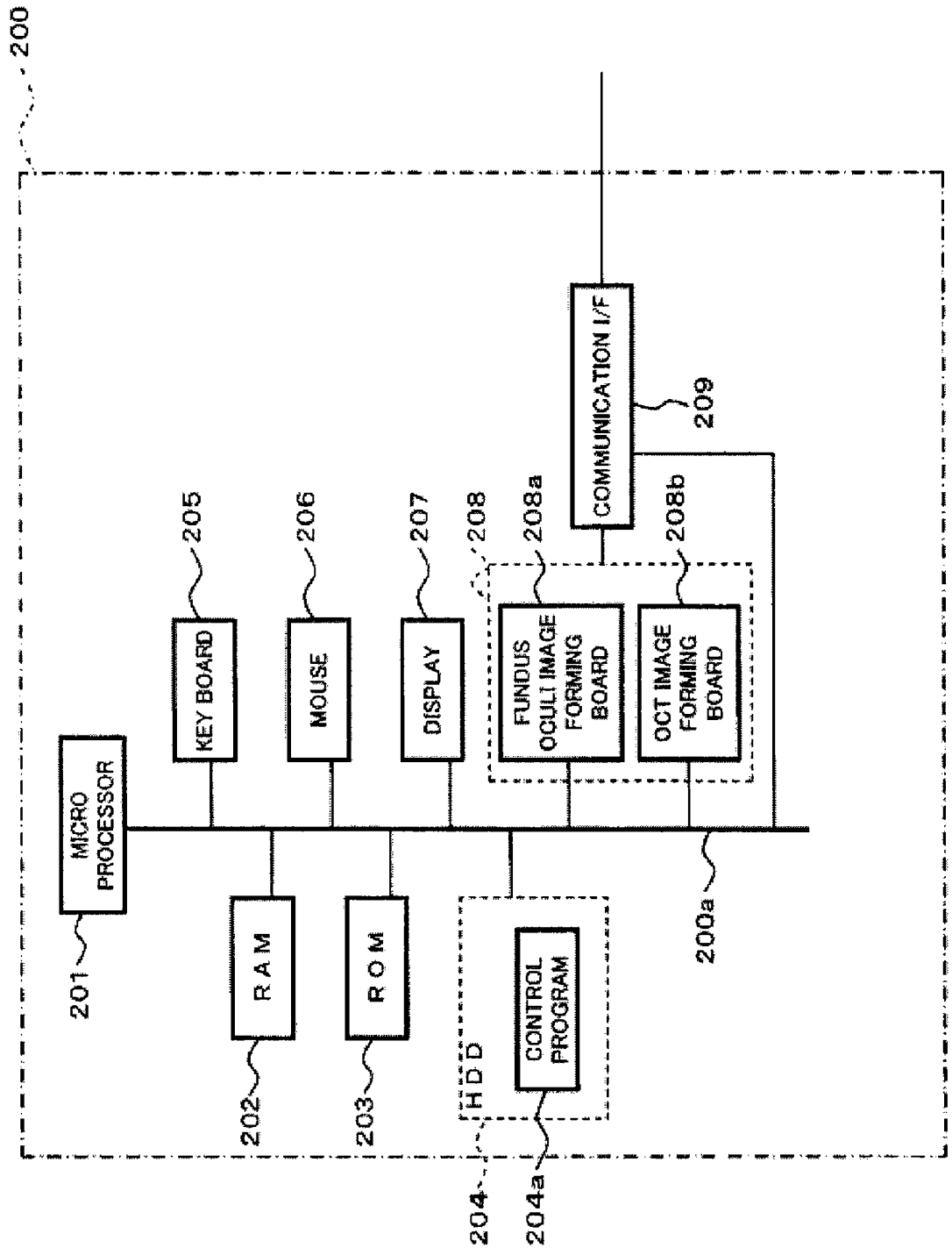
FIG. 4 is a schematic block diagram showing an example of the hardware configuration of an arithmetic control unit in the preferred embodiment of the fundus oculi observation device according to the present invention.
Figure 5:
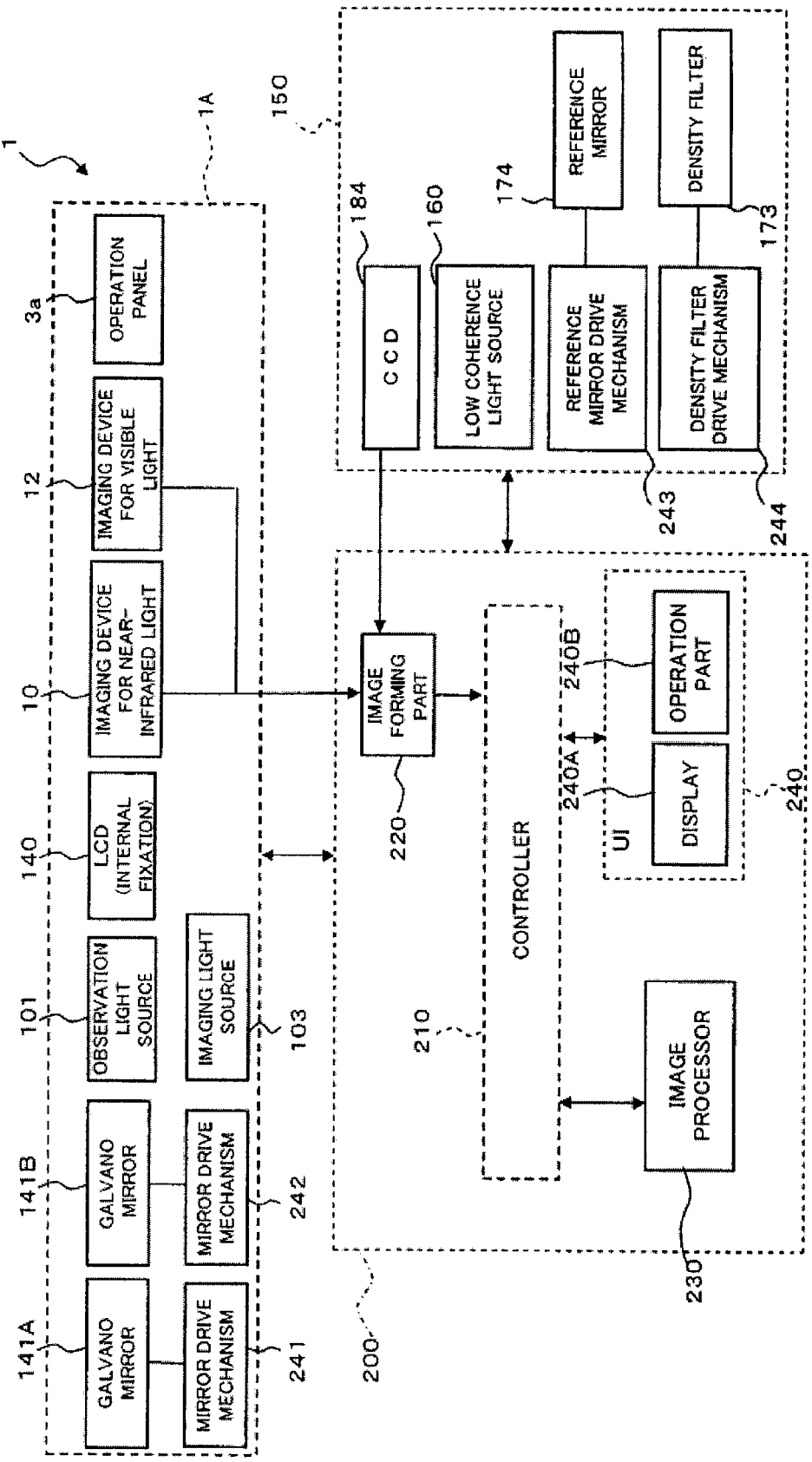
FIG. 5 is a schematic block diagram showing an example of the configuration of a control system in the preferred embodiment of the fundus oculi observation device according to the present invention.
Figure 6:
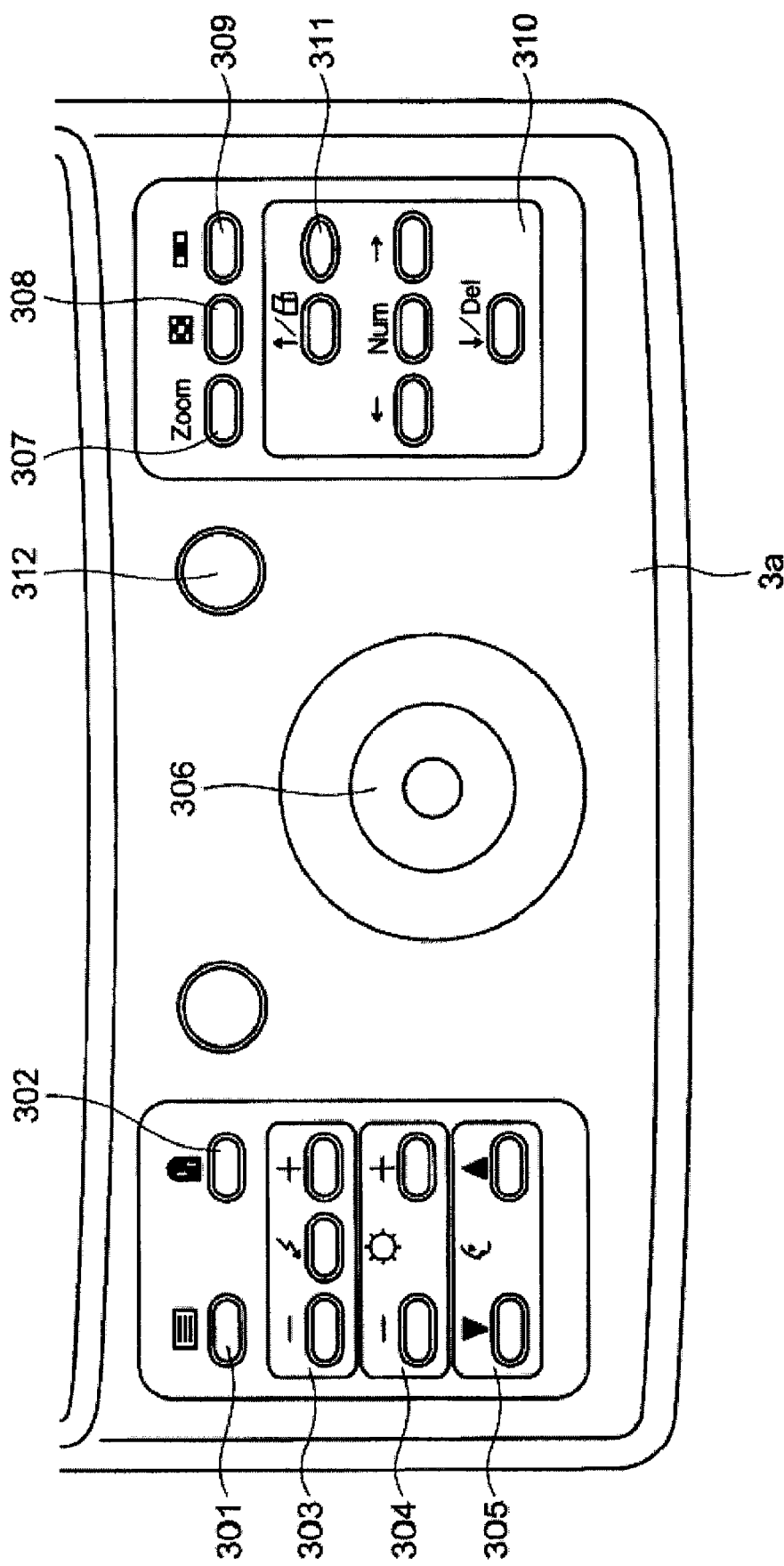
FIG. 6 is a schematic diagram showing an example of the appearance of an operation panel in the preferred embodiment of the fundus oculi observation device according to the present invention.
Figure 7:
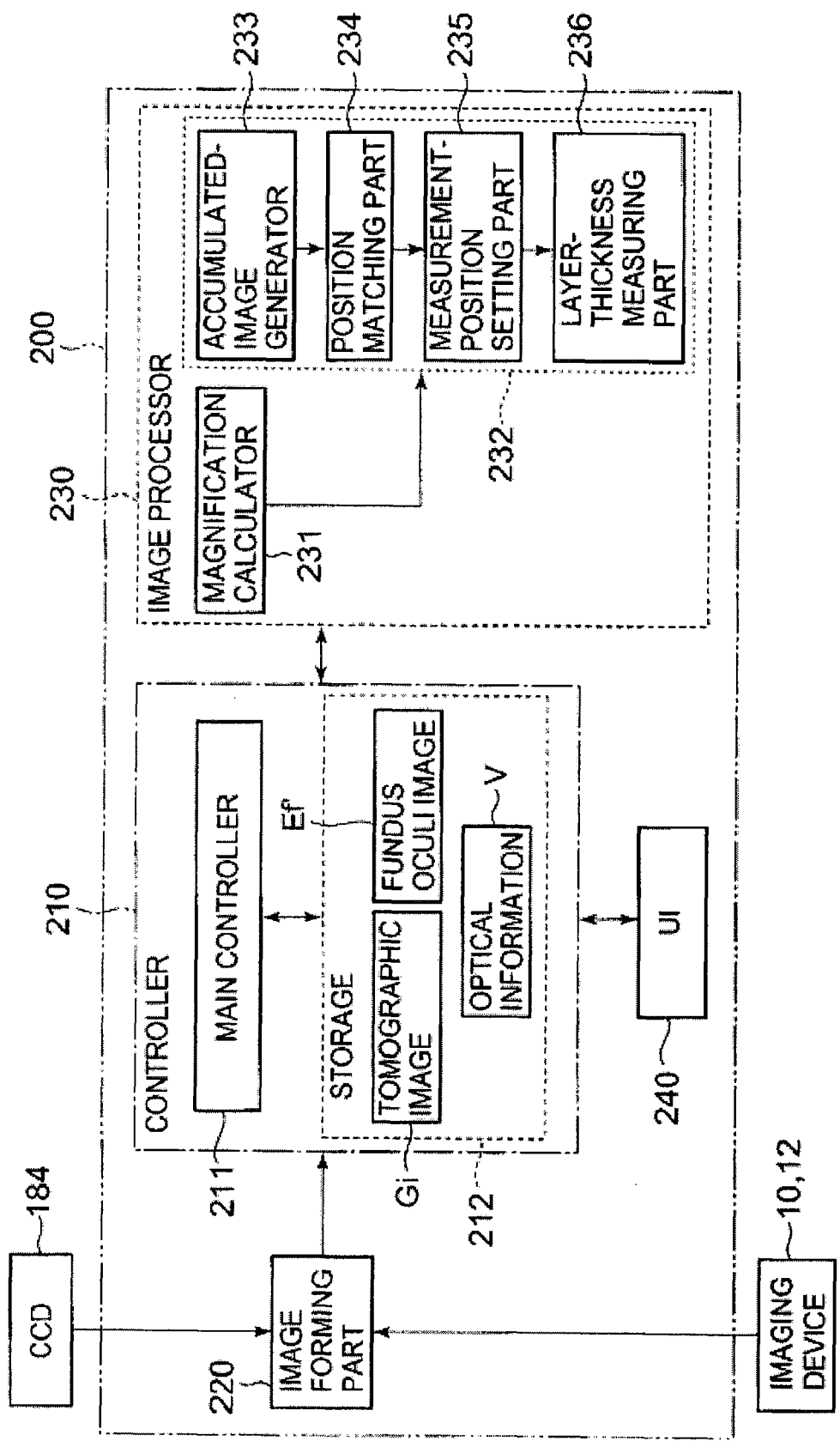
FIG. 7 is a schematic block diagram showing an example of the functional configuration of the arithmetic control unit in the preferred embodiment of the fundus oculi observation device according to the present invention.

First, referring to FIGS. 1-7, the configuration of the fundus oculi observation device according to a first embodiment of the present invention will be described. FIG. 1 shows an example of the entire configuration of a fundus oculi observation device 1 according to the present embodiment. FIG. 2 shows an example of the configuration of a scanning unit 141 in a retinal camera unit 1A. FIG. 3 shows an example of the configuration of an OCT unit 150. FIG. 4 shows an example of the hardware configuration of an arithmetic control unit 200. FIG. 5 shows an example of the configuration of a control system of the fundus oculi observation device 1. FIG. 6 shows an example of the configuration of an operation panel 3a disposed to the retinal camera unit 1A. FIG. 7 shows an example of the configuration of a control system of the arithmetic control unit 200.

[Entire Configuration]

Figure 15:
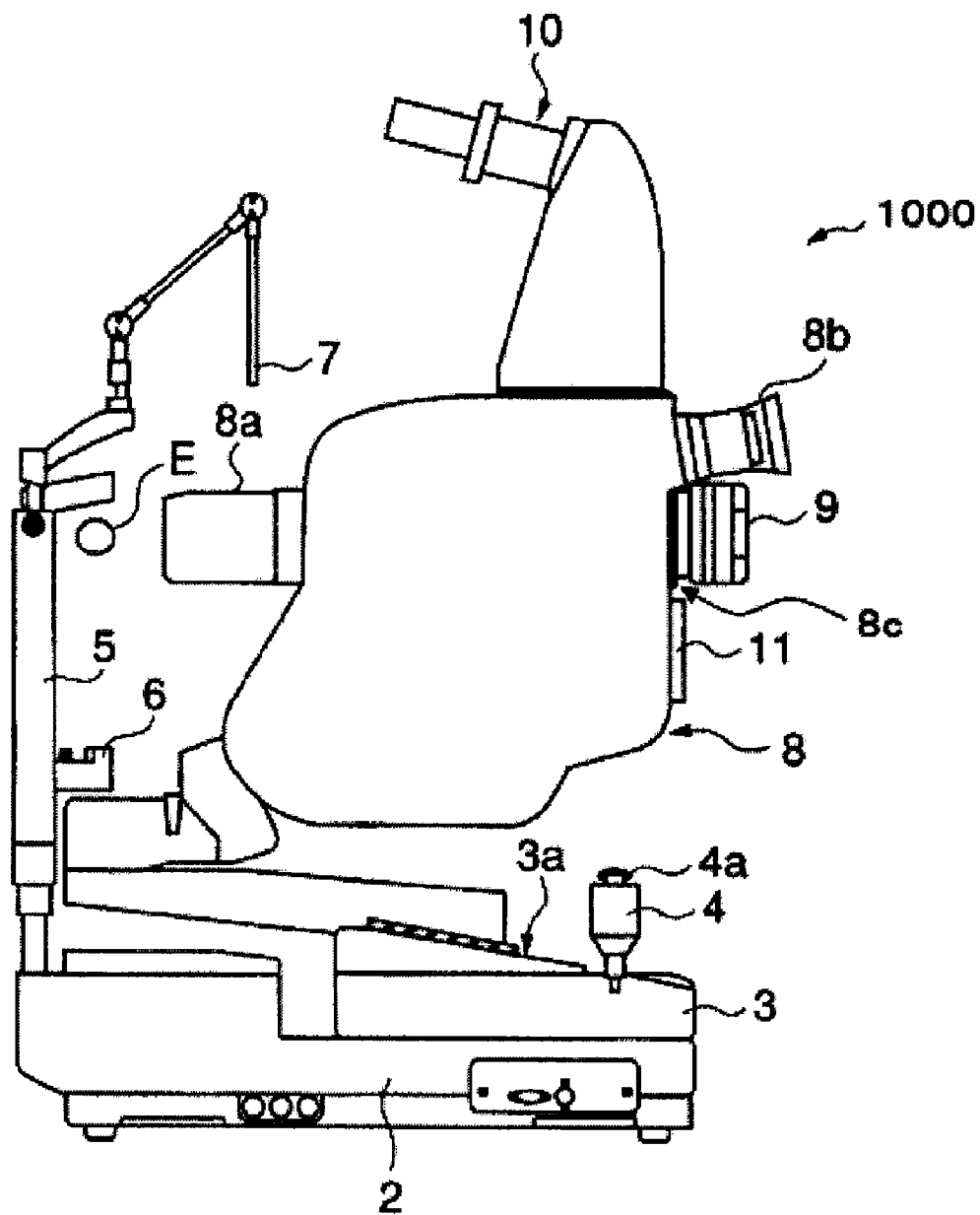
FIG. 15 is a schematic side view showing an example of the appearance of a conventional fundus oculi observation device (retinal camera).
Figure 16:
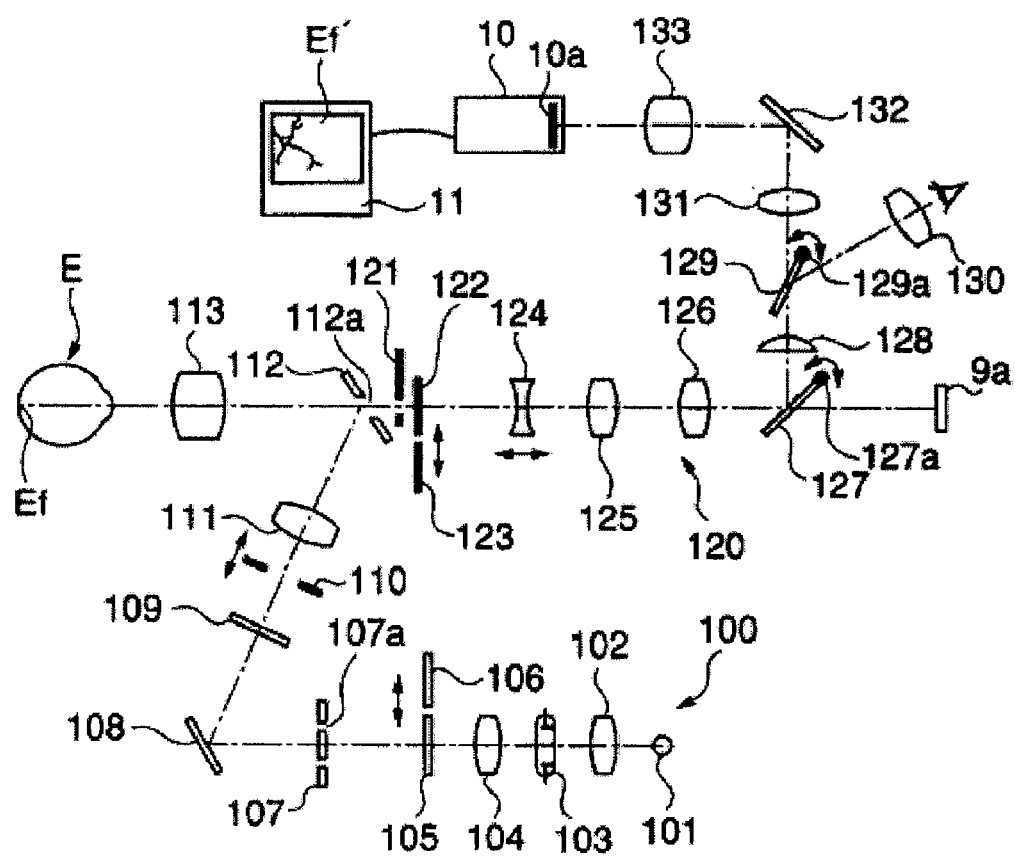
FIG. 16 is a schematic diagram showing an example of the internal configuration (optical system configuration) of a conventional fundus oculi observation device (retinal camera).

As shown in FIG. 1, the fundus oculi observation device 1 according to the present embodiment comprises: the retinal camera unit 1A that has the same function as the retinal camera of FIGS. 15 and 16; the OCT unit 150 accommodating an optical system of an optical image measurement device (OCT device); and the arithmetic control unit 200 that executes various arithmetic processes, control processes, and the like.

To the OCT unit 150, one end of a connection line 152 is attached. To the other end of the connection line 152, a connector part 151 is attached. This connector part 151 is mounted on a mounting part (refer to the mounting part 8c shown in FIG. 15) of a case of the retinal camera unit 1A. Moreover, a conductive optical fiber runs through the inside of the connection line 152. Thus, the OCT unit 150 and the retinal camera unit 1A are optically connected via the connection line 152. An optical system of the OCT unit 150 may be disposed inside the case of the retinal camera unit 1A.

[Configuration of Retinal Camera Unit]

The retinal camera unit 1A is a device configured to capture 2-dimensional images of the surface of the fundus oculi by imaging devices 10 and 12. The retinal camera unit 1A is a device configured to form a 2-dimensional image of the surface of a fundus oculi of an eye, based on optically obtained data (data detected by the imaging devices 10 and 12), and has almost the same appearance as the conventional retinal camera 1000 shown in FIG. 15. As in the conventional optical system shown in FIG. 16, the retinal camera unit 1A is provided with an illumination optical system 100 that illuminates the fundus oculi Ef of the eye E, and an imaging optical system 120 that guides the fundus oculi reflection light of the illumination light to the imaging device 10.

Although the details will be described later, the imaging device 10 in the imaging optical system 120 of the present embodiment detects the illumination light having a wavelength in the near-infrared region. Moreover, this imaging optical system 120 is further provided with the imaging device 12 for detecting the illumination light having a wavelength in the visible region. Moreover, this imaging optical system 120 guides a signal light coming from the OCT unit 150 to the fundus oculi Ef, and guides the signal light passed through the fundus oculi Ef to the OCT unit 150.

As in the conventional one, the illumination optical system 100 comprises: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 emits an illumination light having a wavelength of the visible region included in a range of, for example, about 400 nm thorough 700 nm. Moreover, the imaging light source 103 emits an illumination light having a wavelength of the near-infrared region included in a range of, for example, about 700-800 nm. The near-infrared light emitted from this imaging light source 103 is set so as to have a shorter wavelength than the light used by the OCT unit 150 (described later).

Further, the imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a halfmirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

The imaging optical system 120 according to the present embodiment is different from the conventional imaging optical system 120 shown in FIG. 16 in that the dichroic mirror 134, the half mirror 135, the dichroic mirror 136, the reflection mirror 137, the imaging lens 138, the lens 139 and the LCD 140 are disposed.

The dichroic mirror 134 is configured to reflect the fundus oculi reflection light (having a wavelength included in a range of about 400-800 nm) of the illumination light from the illumination optical system 100, and transmit a signal light LS (having a wavelength included in a range of, for example, about 800-900 nm; described later) from the OCT unit 150.

Further, the dichroic mirror 136 is configured to transmit the illumination light having a wavelength of the visible region from the illumination optical system 100 (a visible light having a wavelength of about 400-700 nm emitted from the observation light source 101), and reflect the illumination light having a wavelength of the near-infrared region (a near-infrared light having a wavelength of about 700-800 nm emitted from the imaging light source 103).

On the LCD 140, a fixation target (internal fixation target) or the like for fixing the eye E is displayed. The light from this LCD 140 is reflected by the half mirror 135 after being converged by the lens 139, and is reflected by the dichroic mirror 136 through the field lens 128. Then, the light passes through the imaging lens 126, the relay lens 125, the variable magnifying lens 124, the aperture mirror 112 (aperture 112a thereof), the objective lens 113 and the like, and enters the eye E. Consequently, an internal fixation target or the like is projected in the fundus oculi Ef of the eye E.

The image pick-up element 10a is an image pick-up element such as a CCD and a CMOS installed in the imaging device 10 such as a TV camera, and is particularly used for detecting light having a wavelength of the near-infrared region (that is, the imaging device 10 is an infrared TV camera for detecting near-infrared light). The imaging device 10 outputs video signals as a result of detection of the near-infrared light.

A touch panel monitor 11 displays a 2-dimensional image (a fundus oculi image Ef') of the surface of the fundus oculi Ef, based on the video signals. The video signals are sent to the arithmetic control unit 200, and the fundus oculi image is displayed on the display (described later).

At the time of imaging of the fundus oculi by the imaging device 10, for example, the illumination light emitted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and is particularly used for detecting light having a wavelength of the visible region (that is, the imaging device 12 is a TV camera for detecting visible light). The imaging device 12 outputs video signals as a result of detection of the visible light.

The touch panel monitor 11 displays a 2-dimensional image (fundus oculi image Ef) of the surface of the fundus oculi Ef, based on the video signals. The video signals are sent to the arithmetic control unit 200, and the fundus oculi image Ef is displayed on the display (described later).

At the time of imaging of the fundus oculi by the imaging device 12, for example, the illumination light emitted from the observation light source 101 of the illumination optical system 100 and having a wavelength of the visible region is used.

The imaging optical system 120 according to the present embodiment is provided with 150 a scanning unit 141 and a lens 142. The scanning unit 141 includes a component for scanning at an application position of the fundus oculi Ef with light emitted from the OCT unit (signal light LS; described later).

The lens 142 makes the signal light LS guided from the OCT unit 150 through the connection line 152 enter the scanning unit 141 in the form of a parallel light flux. Moreover, the lens 142 acts so as to converge the fundus oculi reflection light of the signal light LS passed through the scanning unit 141.

FIG. 2 shows an example of a specific configuration of the scanning unit 141. The scanning unit 141 comprises Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by a drive mechanism described later (mirror drive mechanisms 241 and 242 shown in FIG. 5), whereby the orientations of reflection surfaces thereof (faces reflecting the signal light LS), namely, the positions of the Galvano mirrors 141A and 141B are changed, respectively.

The rotary shafts 141a and 141b are arranged so as to be orthogonal to each other. In FIG. 2, the rotary shaft 141a of the Galvano mirror 141A is arranged in parallel to the paper face of this figure, whereas the rotary shaft 141b of the Galvano mirror 141B is arranged so as to be orthogonal to the paper face of this figure.

That is, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the pair of Galvano mirrors 141A and 141B act so as to change the reflecting directions of the signal light LS to directions orthogonal to each other. As seen from FIGS. 1 and 2, scan with the signal light LS is performed in the x direction when the Galvano mirror 141A is rotated, and scan with the signal light LS is performed in the y direction when the Galvano mirror 141B is rotated.

The signal lights LS reflected by the Galvano mirrors 141A and 141B are reflected by reflection mirrors 141C and 141D, thereby traveling in the same directions as having entered into the Galvano mirror 141A.

As described before, the conductive optical fiber 152a runs through the inside of the connection line 152, and an end face 152b of the optical fiber 152a is arranged facing the lens 142. The signal light LS emitted from this end face 152b travels while expanding its beam diameter toward the lens 142. The light is converged into a parallel light flux by this lens 142. On the contrary, the signal light LS passed through the fundus oculi Ef is converged toward the end face 152b by the lens 142, and guided to the optical fiber 152a.

[Configuration of OCT Unit]

Next, the configuration of the OCT unit 150 will be described referring to FIG. 3. The OCT unit 150 shown in FIG. 3 is a device configured to form a tomographic image of the fundus oculi based on optically obtained data (data detected by a CCD 184 described later).

The OCT unit 150 has almost the same optical system as the conventional optical image measurement device. That is, the OCT unit 150 has: an interferometer that splits the light emitted from the light source into a reference light and a signal light and generates interference light by superposing the reference light passed through a reference object and the signal light passed through a measurement object (fundus oculi Ef); and a part configured to detect this interference light and output signals as the result of the detection (detection signals) toward the arithmetic control unit 200. The arithmetic control unit 200 forms a tomographic image of the measurement object (fundus oculi Ef), by analyzing the detection signals.

A low-coherence light source 160 is composed of a broad-band light source, such as a super luminescent diode (SLD) and a light emitting diode (LED), configured to emit a low-coherence light L0. This low-coherence light L0 is, for example, a light that has a wavelength of the near-infrared region and has a time-wise coherence length of approximately several tens of micrometers.

The low-coherence light L0 has a longer wavelength than the illumination light (wavelength: about 400-800 nm) of the retinal camera unit 1A, for example, a wavelength included in a range of about 800-900 nm.

The low-coherence light L0 emitted from the low-coherence light source 160 is guided to an optical coupler 162 through an optical fiber 161 composed of, for example, a single mode fiber or a PM (Polarization maintaining) fiber. The optical coupler 162 splits this low-coherence light L0 into a reference light LR and the signal light LS.

Although the optical coupler 162 acts as both a part (splitter) for splitting light and a part (coupler) for superposing lights, it will be herein referred to as an "optical coupler" idiomatically.

The reference light LR generated by the optical coupler 162 is guided by an optical fiber 163 composed of a single mode fiber or the like, and emitted from the end face of the fiber. The emitted reference light LR is converged into a parallel light flux by a collimator lens 171, passed through a glass block 172 and a density filter 173, and then reflected by a reference mirror 174 (reference object).

The reference light LR reflected by the reference mirror 174 is converged to the fiber end face of the optical fiber 163 by the collimator lens 171 again through the density filter 173 and the glass block 172. The converged reference light LR is guided to the optical coupler 162 through the optical fiber 163.

The glass block 172 and the density filter 173 act as a delaying part for making the optical path lengths (optical distances) of the reference light LR and the signal light LS coincide, and also as a dispersion correction part for making the dispersion characteristics of the reference light LR and the signal light LS coincide.

Further, the density filter 173 also acts as a dark filter for reducing the amount of the reference light, and is composed of a rotating ND (neutral density) filter, for example. This density filter 173 acts so as to change the reduction amount of the reference light LR by being rotary driven by a drive mechanism including a drive unit such as a motor (a density filter drive mechanism 244 described later; refer to FIG. 5). Consequently, it is possible to change the amount of the reference light LR contributing to generation of the interference light LC.

Furthermore, the reference mirror 174 is configured so as to move in the traveling direction (the direction of the arrow pointing both sides shown in FIG. 3) of the reference light LR. As a result, the optical path length of the reference light LR according to the axial length of the eye E, etc. is ensured. The reference mirror 174 is moved by a drive mechanism (a reference mirror driving mechanism 243 described later; ref. FIG. 5) including a driving part such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A. Then, the signal light LS enters into the eye E through the lens 142, the scanning unit 141, the dichroic mirror 134, the imaging lens 126, the relay lens 125, the variable magnifying lens 124, the imaging diaphragm 121, the aperture 112a of the aperture mirror 112, and the objective lens 113. The barrier filter 122 and 123 are retracted from the optical path in advance, respectively, when the signal light LS is made to enter the eye E.

The signal light LS having entered the eye E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS passed through the fundus oculi Ef is a light containing information reflecting the state of the surface of the fundus oculi Ef and information reflecting the state of backscatter at the refractive index boundary of the deep area tissue of the fundus oculi Ef. This light may be simply referred to as "fundus oculi reflection light of the signal light LS."

The fundus oculi reflection light of the signal light LS travels reversely on the above path within the retinal camera unit 1A to be converged at the end face 152b of the optical fiber 152a, enters into the OCT unit 150 through the optical fiber 152a, and returns to the optical coupler 162 through the optical fiber 164.

The optical coupler 162 superimposes the signal light LS returning through the fundus oculi Ef and the reference light LR reflected by the reference mirror 174, thereby generating the interference light LC. The generated interference light LC is guided into a spectrometer 180 through an optical fiber 165 composed of a single mode fiber or the like.

Herein, although a Michelson-type interferometer is adopted in the present embodiment, for instance, a Mach Zender type, etc. and any type of interferometer may be adopted appropriately.

The spectrometer 180 comprises a collimator lens 181, a diffraction grating 182, an image forming lens 183, and a CCD 184. The diffraction grating 182 in the present embodiment is a transmission-type diffraction grating that transmits light; however, needless to say, a reflection-type diffraction grating that reflects light may also be used. Moreover, needless to say, it is also possible to adopt, in place of the CCD 184, other photo-detecting elements.

The interference light LC having entered the spectrometer 180 is split (resolved into spectra) by the diffraction grating 182 after converged into a parallel light flux by the collimator lens 181. The split interference light LC forms an image on the image pick-up surface of the CCD 184 by the image forming lens 183. The CCD 184 receives the interference light LC and converts to electrical detection signals, and outputs the detection signals to the arithmetic control unit 200.

[Configuration of Arithmetic Control Unit]

Next, the configuration of the arithmetic control unit 200 will be described. This arithmetic control unit 200 corresponds to an example of the "fundus oculi image processing device" according to the present invention.

The arithmetic control unit 200 performs a process of analyzing the detection signals inputted from the CCD 184 of the spectrometer 180 of the OCT unit 150, and forming tomographic images of the fundus oculi Ef of the eye E. A technique for this analysis is the same as a conventional technique for the Fourier domain OCT.

Further, the arithmetic control unit 200 performs a process of forming (image data of) a 2-dimensional image showing the state of the surface (retina) of the fundus oculi Ef, based on the video signals outputted from the imaging devices 10 and 12 of the retinal camera unit 1A.

Furthermore, the arithmetic control unit 200 executes control of each part of the retinal camera unit 1A and the OCT unit 150.

Control of the retinal camera unit 1A is, for example: control of emission of illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of shift of the illumination diaphragm 110 (control of the diaphragm value); control of the diaphragm value of the imaging diaphragm 121; and control of shift of the variable magnifying lens 124 (control of the magnification). Moreover, the arithmetic control unit 200 executes control of the operation of the Galvano mirrors 141A and 141B inside the scanning unit 141 (operation of changing the directions of the reflection faces).

Further, control of the OCT unit 150 is, for example: control of emission of the low-coherence light L0 by the low-coherence light source 160; control of shift of the reference mirror 174; control of the rotary operation of the density filter 173 (operation of changing the reduction amount of the reference light LR); and control of the accumulated time of the CCD 184.

An example of the hardware configuration of the arithmetic control unit 200 that acts as described above will be described referring to FIG. 4.

The arithmetic control unit 200 is provided with the same hardware configuration as that of a conventional computer. To be specific, the arithmetic control unit 200 comprises: a microprocessor 201 (CPU, MPU, etc.), a RAM202, a ROM203, a hard disk drive (HDD) 204, a keyboard 205, a mouse 206, a display 207, an image forming board 208, and a communication interface (I/F) 209. These parts are connected via a bus 200a.

The microprocessor 201 executes operations characteristic to the present embodiment, by loading a control program 204a stored in the hard disk drive 204, onto the RAM202.

Further, the microprocessor 201 executes control of each part of the device described above, various arithmetic processes, etc. Moreover, the microprocessor 201 executes control of each part of the device corresponding to an operation signal from the keyboard 205 or the mouse 206, control of a display process by the display 207, and control of a transmission/reception process of various data, control signals and so on by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is any display device composed of an LCD, a CRT (Cathode Ray Tube) display or the like. The display 207 displays various images of the fundus oculi Ef formed by the fundus oculi observation device 1, and displays various screens such as an operation screen and a set-up screen.

The user interface of the fundus oculi observation device 1 is not limited to the above configuration, and may be configured by using any user interface having a function of displaying and outputting various information, and a function of inputting various information and operating the device, such as a track ball, a control lever, a touch panel type of LCD, and a control panel for ophthalmology examinations.

The image forming board 208 is a dedicated electronic circuit for a process of forming (image data of) images of the fundus oculi Ef of the eye E. This image forming board 208 is provided with a fundus oculi image forming board 208a and an OCT image forming board 208b.

The fundus oculi image forming board 208a is a dedicated electronic circuit that operates to form image data of fundus oculi images based on the video signals from the imaging device 10 and the imaging device 12 of the retinal camera unit 1A.

Further, the OCT image forming board 208b is a dedicated electronic circuit that operates to form image data of tomographic images of the fundus oculi Ef, based on the detection signals from the CCD 184 of the spectrometer 180 in the OCT unit 150.

By providing the image forming board 208, it is possible to increase the processing speed for forming image data of fundus oculi images and tomographic images.

The communication interface 209 performs a process of sending control signals from the microprocessor 201, to the retinal camera unit 1A or the OCT unit 150. Moreover, the communication interface 209 performs a process of receiving video signals from the imaging devices 10 and 12 of the retinal camera unit 1A and detection signals from the CCD 184 of the OCT unit 150, and inputting the signals to the image forming board 208. At this time, the communication interface 209 operates to input the video signals from the imaging devices 10 and 12, to the fundus oculi image forming board 208a, and input the detection signal from the CCD 184, to the OCT image forming board 208b.

Further, in a case where the arithmetic control unit 200 is connected to a network such as a LAN (Local Area Network) and the Internet, it is possible to configure so as to be capable of data communication via the network, by providing the communication interface 209 with a network adapter like a LAN card or communication equipment like a modem. In this case, by mounting a server accommodating the control program 204a on the network, and at the same time, configuring the arithmetic control unit 200 as a client terminal of the server, it is possible to cause the fundus oculi observation device 1 to execute the operation according to the present invention.

[Configuration of Control System]

Next, the configuration of the control system of the fundus oculi observation device 1 will be described referring to FIGS. 5-7.

(Controller)

The control system of the fundus oculi observation device 1 is configured mainly having a controller 210 of the arithmetic control unit 200 shown in FIG. 5. The controller 210 comprises the microprocessor 201, the RAM202, the ROM203, the hard disk drive 204 (control program 204a), and the communication interface 209.

The controller 210 executes the aforementioned controlling processes through the microprocessor 201 operating based on the control program 204a. In specific, for the retinal camera unit 1A, the controller 210 performs control of the mirror drive mechanisms 241 and 242 for changing the positions of the Galvano mirrors 141A and 141B, control of the display operation of the internal fixation target by the LCD 140, etc.

Further, for the OCT unit 150, the controller 210 performs control of the low-coherence light source 160 and the CCD 184, control of the density filter drive mechanism 244 for rotating the density filter 173, control of the reference mirror drive mechanism 243 for moving the reference mirror 174 in the traveling direction of the reference light LR, etc.

Furthermore, the controller 210 performs control for causing the display 240A of the user interface (UI) 240 to display two kinds of images photographed by the fundus oculi observation device 1: that is, a 2-dimensional image (fundus oculi image Ef') of the surface of the fundus oculi Ef obtained by the retinal camera unit 1A, and a tomographic image of the fundus oculi Ef formed based on the detection signals obtained by the OCT unit 150. These images may be displayed on the display 240A separately, or may be displayed side by side simultaneously. The details of the configuration of the controller 210 will be described later, based on FIG. 7.

(Image forming Part)

An image forming part 220 performs a process of forming image data of the fundus oculi image based on the video signals from the imaging devices 10 and 12 of the retinal camera unit 1A. Moreover, the image forming part 220 performs a process of forming image data of the tomographic images of the fundus oculi Ef based on the detection signals from the CCD 184 of the OCT unit 150. The imaging forming part 220 comprises the imaging forming board 208 and the communication interface 209. In this specification, "image" may be identified with "image data" corresponding thereto.

Each part of the retinal camera unit 1A for acquiring a tomographic image of the fundus oculi Ef, the OCT unit 150, the image forming part 220 (OCT image forming board 208b), and the image processor 230 constitute an example of the "image forming part" configured to form tomographic images of the fundus oculi Ef. Moreover, the image forming part in the present embodiment includes each part of the retinal camera unit 1A for acquiring 2-dimensional images of the surface of the fundus oculi Ef, and the image forming part 220 (fundus oculi image forming board 208a).

(Image Processor)

The image processor 230 applies various image processing to image data of images formed by the image forming part 220. For example, the image processor 230 executes a process of forming image data of a 3-dimensional image of the fundus oculi Ef based on the tomographic images corresponding to the detection signal from the OCT unit 150, and various correction processes such as brightness correction and dispersion correction of the images.

Herein, image data of a 3-dimensional image is image data made by assigning pixel values to each of a plurality of voxels arranged 3-dimensionally, and is referred to as volume data, voxel data, and the like. When displaying an image based on volume data, the image processor 230 operates to apply a rendering process (such as volume rendering and MIP (Maximum Intensity Projection)) to this volume data and form image data of a pseudo 3-dimensional image seen from a specified viewing direction. On the display 240A, the pseudo 3-dimensional image based on the image data is displayed.

Further, the image processor 230 executes a process for obtaining the position of each kind of layer of the fundus oculi Ef included in tomographic images. Here, the position of the layer is information representing the position of a specific layer of the fundus oculi Ef on a tomographic image, such as the position on a tomographic image corresponding to a specific layer of the fundus oculi Ef, and the position on a tomographic image corresponding to the border with an adjacent layer. Moreover, based on the obtained position of the layer, the image processor 230 calculates the thickness of the layer. These processes will be described in detail in the explanation of FIG. 7.

The image processor 230 comprises the microprocessor 201, the RAM 202, the ROM 203, and the hard disk drive 204 (control program 204a).

(User Interface)

The user interface (UI) 240 comprises the display 240A and an operation part 240B. The display 240A is composed of a display device such as the display 207. Further, the operation part 240B is composed of an input device or an operation device such as the keyboard 205 and the mouse 206.

(Operation Panel)

The operation panel 3a of the retinal camera unit 1A will be described below. As shown in FIG. 15, this operation panel 3a is arranged on the platform 3 of the retinal camera unit 1A, for example.

The operation panel 3a according to the present embodiment is, different from the conventional configuration described in Background of the Invention, provided with an operating part used to instruct an operation for capturing an image of the surface of the fundus oculi Ef and the vicinity thereof, and an operating part used to instruct an operation for capturing a tomographic image of the fundus oculi Ef (in the conventional configuration, only the former operating part is provided).

In the present embodiment, placement of the operation panel 3a makes it possible to execute an operation for capturing various images in the same manner as when operating a conventional retinal camera.

As shown in FIG. 6, the operation panel 3a is provided with, for example, a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a certain menu screen for a user to select and designate various menus (such as an imaging menu for imaging a 2-dimensional image of the surface of the fundus oculi Ef, a tomographic image and the like, and a setting menu for inputting various settings).

When this menu switch 301 is operated, the operation signal is inputted to the controller 210. The controller 210 causes the touch panel monitor 11 or the display 240A to display a menu screen, in response to the input of the operation signal. A controller (not shown) may be provided in the retinal camera unit 1A, whereby the controller causes the touch panel monitor 11 to display the menu screen.

The split switch 302 is a switch operated to switch the light on and off of the split bright line for focusing (e.g., see JP Patent laid-open No. H9-66031. Also referred to as split target, split mark and so on.). The configuration for projecting this split bright line onto the eye E (split bright line projection part) is housed, for example, in the retinal camera unit 1A (not shown in FIG. 1).

When this split switch 302 is operated, the operation signal is inputted to the controller 210 (or the aforementioned controller inside the retinal camera unit 1A; the same hereinafter). The controller 210 projects the split bright line onto the eye E by controlling the split bright line projection part, in response to the input of this operation signal.

The imaging light amount switch 303 is a switch operated to adjust the emitted light amount of the imaging light source 103 (photographing light amount) depending on the state of the eye E (such as the degree of opacity of the lens). This imaging light amount switch 303 is provided with, for example, a photographing light amount increasing switch "+" for increasing the photographing light amount, a photographing light amount decreasing switch "−" for decreasing the photographing light amount, and a reset switch (a button in the middle) for setting the photographing light amount to a predetermined initial value (default value).

When one of the imaging light amount switches 303 is operated, the operation signal is inputted to the controller 210. The controller 210 controls the imaging light source 103 in response to the inputted operation signal and adjusts the photographing light amount.

The observation light amount switch 304 is a switch operated to adjust the emitted light amount (observation light amount) of the observation light source 101. The observation light amount switch 304 is provided with, for example, an observation light amount increasing switch "+" for increasing the observation light amount, and an observation light amount decreasing switch "−" for decreasing the observation light amount.

When one of the observation light amount switches 304 is operated, the operation signal is inputted to the controller 210. The controller 210 controls the observation light source 101 in response to the inputted operation signal and adjusts the observation light amount. The jaw holder switch 305 is a switch to move the position of the jaw holder 6 shown in FIG. 15. This jaw holder switch 305 is provided with, for example, an upward movement switch (upward triangle) for moving the jaw holder 6 upward, and a downward movement switch (downward triangle) for moving the jaw holder 6 downward.

When one of the jaw holder switches 305 is operated, the operation signal is inputted to the controller 210. The controller 210 controls a jaw holder movement mechanism (not shown) in response to the inputted operation signal and moves the jaw holder 6 upward or downward.

The photographing switch 306 is a switch used as a trigger switch for capturing a 2-dimensional image of the surface of the fundus oculi Ef or a tomographic image of the fundus oculi Ef.

When the photographing switch 306 is operated in a state where a menu to photograph a 2-dimensional image is selected, the controller 210 that has received the operation signal controls the imaging light source 103 to emit photographing illumination light, and also causes the display 240A or the touch panel monitor 11 to display a 2-dimensional image of the surface of the fundus oculi Ef, based on the video signal outputted from the imaging device 10 having detected the fundus oculi reflection light.

On the other hand, when the photographing switch 306 is operated in a state where a menu to capture a tomographic image is selected, the controller 210 that has received the operation signal controls the low-coherence light source 160 to emit the low-coherence light L0, and also controls the Galvano mirrors 141A and 141B to scan the signal light LS. Moreover, the controller 210 causes the display 240A or the touch panel monitor 11 to display a tomographic image of the fundus oculi Ef formed by the image forming part 220 (and image processor 230), based on the detection signal outputted from the CCD 184 that has detected the interference light LC.

The zoom switch 307 is a switch operated to change the angle of view (zoom magnification) at the time of photographing of the fundus oculi Ef. Every time this zoom switch 307 is operated, the photographing angle is set alternately to 45 degrees and 22.5 degrees, for example.

When this zoom switch 307 is operated, the controller 210 that has received the operation signal controls a variable magnifying lens driving mechanism (not shown) to move the variable magnifying lens 124 in the optical axis direction of the imaging optical system 120, thereby changing the photographing angle of view.

The image switching switch 308 is a switch operated to switch displayed images. When the image switching switch 308 is operated in a state where a fundus oculi observation image (a 2-dimensional image of the surface of the fundus oculi Ef based on the video signal from the imaging device 12) is displayed on the display 240A or the touch panel monitor 11, the controller 210 having received the operation signal controls the display 240A or touch panel monitor 11 to display the tomographic image of the fundus oculi Ef.

On the other hand, when the image switching switch 308 is operated in a state where a tomographic image of the fundus oculi is displayed on the display 240A or the touch pane monitor 11, the controller 210 having received the operation signal controls the display 240A or the touch panel monitor 11 to display the fundus oculi observation image.

The fixation target switching switch 309 is a switch operated to switch the position of the internal fixation target displayed by the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi (fixation position for fundus oculi center imaging)," "fixation position to capture the image of the peripheral region of macula lutea (fixation position for macula lutea imaging)" and "fixation position to capture the image of the peripheral region of papilla (fixation position for papilla imaging)," in a circulative fashion.

In response to the operation signals from the fixation target switching switch 309, the controller 210 causes the LCD 140 to display the internal fixation target in different positions on the display surface thereof. The display positions of the internal fixation target corresponding to the above three fixation positions, for example, can be preset based on clinical data, or can be set for each eye E (image of the fundus oculi Ef) in advance.

The fixation target position adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a predetermined initial position (default position).

Upon reception of the operation signal from either of these switches of the fixation target position adjusting switch 310, the controller 210 controls the LCD 140 to move the display position of the internal fixation target, in response to the operation signal.

The fixation target size switching switch 311 is a switch operated to change the size of the internal fixation target. When this fixation target size switching switch 311 is operated, the controller 210 that has received the operation signal controls the LCD 140 to change the display size of the internal fixation target. The display size of the internal fixation target can be switched, for example, between "normal size" and "enlarged size," alternately. As a result, the size of the projection image of the fixation target projected onto the fundus oculi Ef is changed. Upon reception of the operation signal from the fixation target position adjusting switch 311, the controller 210 controls the LCD 140 to change the display size of the internal fixation target, in response to the operation signal.

The mode switching knob 312 is a knob rotationally operated to select various photographing modes, such as a fundus oculi photographing mode to photograph a 2-dimensional image of the fundus oculi Ef, a B-scan mode to perform B-scan of the signal light LS, and a 3-dimensional scan mode to scan with the signal light LS 3-dimensionally. In addition, the mode switching knob 312 may be configured so as to be capable of selecting a replay mode to replay and display a captured 2-dimensional image or tomographic image of the fundus oculi Ef. In addition, it may be configured so as to be capable of selecting a photographing mode to control so that the photographing of the fundus oculi Ef would be performed immediately after scanning of the signal light LS. Control of each part of the device for causing the fundus oculi observation device 1 to execute the operation corresponding to the each mode is executed by the controller 210.

Herein, the feature of control of scanning of the signal light LS by the controller 210, and the feature of processing to the detection signal from the OCT unit 150 by the image forming part 220 and the image processor 230 will be respectively described. An explanation regarding the process by the image forming part 220, etc., to the video signal from the retinal camera unit 1A will be omitted because it is the same as the conventional process.

[Signal Light Scanning]

Scanning of the signal light LS is performed by changing the positions (directions of the reflecting surfaces) of the Galvano mirrors 141A and 141B of the scanning unit 141 in the retinal camera unit 1A. By controlling the mirror drive mechanisms 241 and 242 respectively to change the directions of the reflecting surfaces of the Galvano mirrors 141A and 141B respectively, the controller 210 scans the application position of the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. Whereas, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling these two Galvano mirrors 141A and 141B, it is possible to scan the signal light LS in any direction on the x-y plane.

Figure 8A:
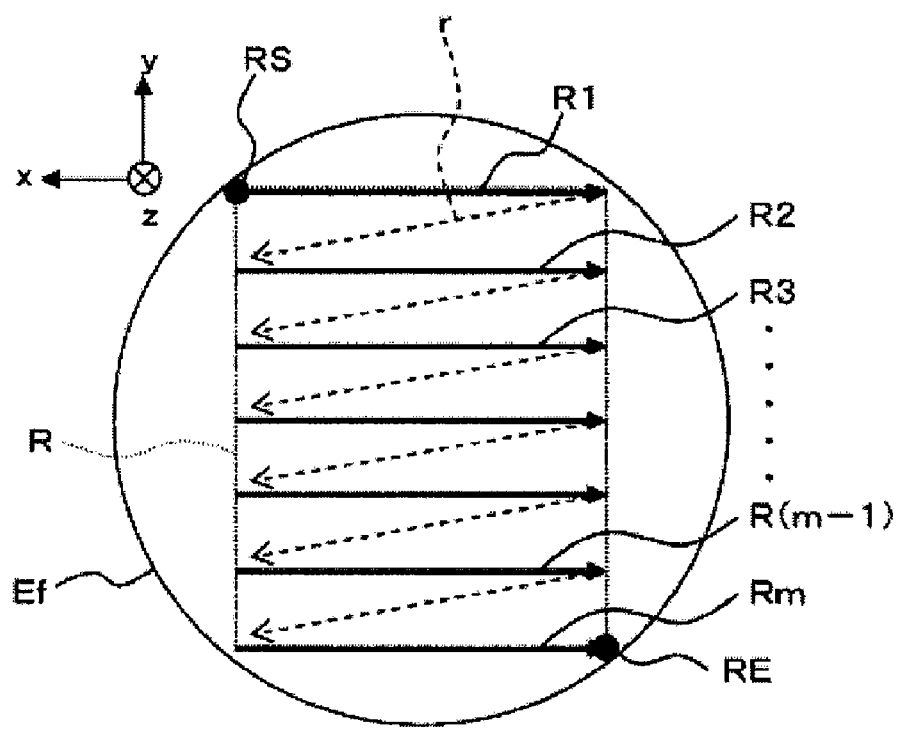
FIGS. 8A and 8B are schematic diagrams showing an example of the feature of scan with a signal light in the preferred embodiment of the fundus oculi observation device according to the present invention.
Figure 8B:
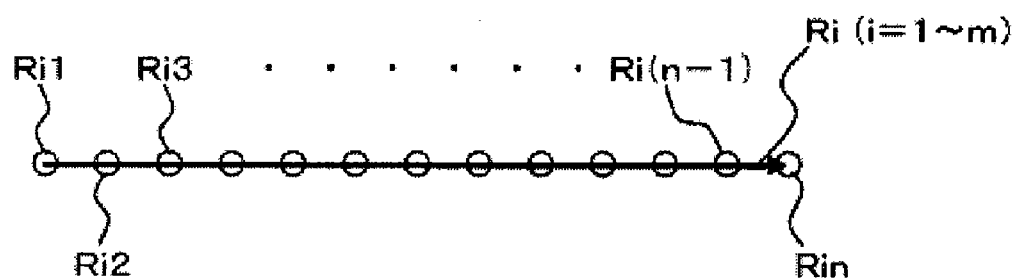

FIGS. 8A and 8B shows an example of the feature of scanning of the signal light LS for forming images of the fundus oculi Ef. FIG. 8A shows an example of the feature of scanning of the signal light LS, when the fundus oculi Ef is seen from a direction that the signal light LS enters the eye E (that is, seen from −z side toward +z side in FIG. 1). Further, FIG. 8B shows an example of the feature of arrangement of scanning points (positions at which image measurement is carried out; target positions of the signal light LS) on each scanning line on the fundus oculi Ef.

As shown in FIG. 8A, the signal light LS is scanned within a rectangular-shaped scanning region R that has been preset. Within this scanning region R, a plurality of (m number of) scanning lines R1-Rm are set in the x-direction. When the signal light LS is scanned along the respective scanning lines Ri (i=1-m), detection signals of the interference light LC are generated.

Herein, a direction of each scanning line Ri will be referred to as the "main scanning direction" and a direction orthogonal thereto will be referred to as the "sub-scanning direction". Accordingly, scanning of the signal light LS in the main scanning direction is performed by changing the facing direction of the reflecting surface of the Galvano mirror 141A, and scanning in the sub-scanning direction is performed by changing the facing direction of the reflecting surface of the Galvano mirror 141 B.

On each scanning line Ri, as shown in FIG. 8B, a plurality of (n number of) scanning points Ri1-Rin are preset.

In order to execute the scanning shown in FIGS. 8A and 8B, the controller 210 firstly controls the Galvano mirrors 141A and 141B to set the target of the signal light LS entering into the fundus oculi Ef to a scan start position RS (scanning point R11) on the first scanning line R1. Subsequently, the controller 210 controls the low-coherence light source 160 to flush the low-coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan the signal light LS in the main scanning direction and set the incident target of the signal light LS to a scanning point R12, and makes the low-coherence light L0 flushed to make the signal light LS enter into the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in response to the interference light LC for each scanning point, by flushing the low-coherence light L0 at each scanning point while shifting the incident target of the signal light LS from scanning point R13 to R14, - - -, R1 (n-1), and R1n in order.

When the measurement at the last scanning point R1n of the first scanning line R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2j (j=1-n) of this second scanning line R2, detection signals corresponding to the respective scanning points R2j are obtained.

Likewise, the measurement is conducted for each of the third scanning line R3, - - -, the m-1th scanning line R(m-1), the mth scanning line Rm to obtain the detection signals corresponding to the respective scanning points. Symbol RE on a scanning line Rm is a scan end position corresponding to a scanning point Rmn.

As a result, the controller 210 obtains m×n number of detection signals corresponding to m×n number of scanning points Rij (i=1-m, j=1-n) within the scanning region R. Hereinafter, a detection signal corresponding to the scanning point Rij may be represented by Dij.

Such interlocking control of the shift of scanning points and the emission of the low-coherence light L0 can be realized by synchronizing, for instance, timing for transmission of control signals to the mirror drive mechanisms 241 and 242 and timing for transmission of control signals (output request signals) to the low-coherence light source 160.

As described above, when each of the Galvano mirrors 141A and 141B is operated, the controller 210 stores the position of each scanning line Ri and the position of each scanning point Rij (coordinates on the x-y coordinate system) as information representing the content of the operation. This stored content (scanning point coordinate information) is used in an image forming process as in conventional one.

[Image Processing]

Next, an example of a process on OCT images (tomography images of the fundus oculi Ef) by the image forming part 220 and the image processor 230 will be described.

The image forming part 220 executes the formation process of tomographic images of the fundus oculi Ef along each scanning line Ri (main scanning direction). Further, the image processor 230 executes the formation process of a 3-dimensional image of the fundus oculi Ef based on these tomographic images formed by the image forming part 220, etc.

The formation process of a tomographic image by the image forming part 220, as in the conventionally one, includes a 2-step arithmetic process. In the first step of the arithmetic process, based on a detection signal Dij corresponding to each scanning point Rij, an image in the depth-wise direction (z-direction in FIG. 1) of the fundus oculi Ef at the scanning point Rij is formed.

Figure 9:
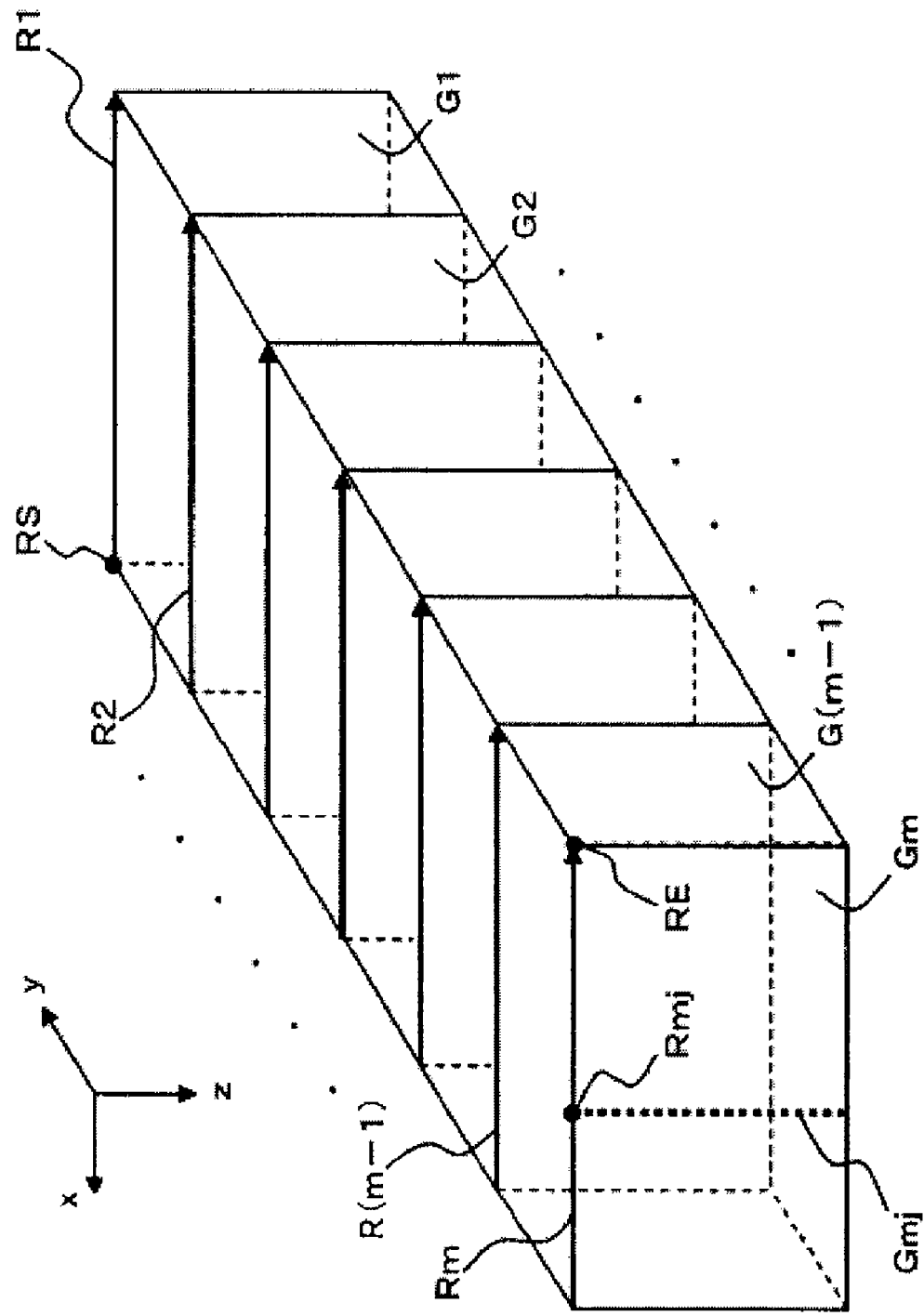
FIG. 9 is a schematic diagram showing an example of the feature of scan with a signal light and the feature of a tomographic image formed along each scanning line in the preferred embodiment of the fundus oculi observation device according to the present invention.

FIG. 9 shows a feature of (a group of) tomographic images formed by the image forming part 220. In the second step of the arithmetic process, for each scanning line Ri, a tomographic image Gi of the fundus oculi Ef along the scanning line Ri is formed, based on the images in the depth-wise direction at the n number of scanning points Ri1-Rin. Then, the image forming part 220 determines the arrangement and distance of the scanning points Ri1-Rin referring to the positional information (scanning point coordinate information described before) of the scanning points Ri1-Rin, and forms a tomographic image Gi along this scanning line Ri.

Through the above process, m number of tomographic images G1-Gm at different positions in the sub-scanning direction (y-direction) are obtained.

Next, a process of forming a 3-dimensional image of the fundus oculi Ef by the image processor 230 will be explained. A 3-dimensional image of the fundus oculi Ef is formed based on the m number of tomographic images G1-Gm obtained through the above arithmetic process. The image processor 230 forms a 3-dimensional image of the fundus oculi Ef by performing a known interpolation process of interpolating an image between the adjacent tomographic images Gi and G(i+1).

At this moment, the image processor 230 determines the arrangement and the distance of each scanning line Ri while referring to the positional information of each scanning line Ri to form this 3-dimensional image. For this 3-dimensional image, a 3-dimensional coordinate system (x, y, z) is set, based on the positional information (the scanning point coordinate information) of each scanning point Rij and the z-coordinate in the depth-wise image.

Further, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depth-wise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

Here, an image Gmj shown in FIG. 9 represents an image in the depth-wise direction (z-direction) at the scanning point Rmj on the scanning line Rm. A depth-wise image at each scanning point Rij on the scanning line Ri formed by the first-step arithmetic process is represented as "image Gij."

[Configuration Details of the Arithmetic Control Device]

The configuration of the arithmetic control device 200 will be described in detail referring to FIG. 7. Here, the controller 210 and image processor 230 of the arithmetic control device 200 will be described in detail specifically.

(Controller)

The controller 210 of the arithmetic control device 200 includes a main controller 211 and a storage 212. The main controller 211 executes the aforementioned various kinds of control processes by the controller 210. Moreover, the main controller 211 executes a process of storing data into the storage 212, and a process of reading out data stored in the storage 212.

The storage 212 stores an image such as a tomographic image Gi (i=1-m) and a fundus oculi image Ef'. Moreover, the storage 212 stores optical information V.

The optical information V includes information on the ocular optical system of the eye E. To be specific, the optical information V includes measured values of the corneal curvature (radius of curvature), refractive power and axial length of the eye E, etc. Here, as the measured value of the refractive power, it is possible to use, for example, a value "S+C/2" obtained from a measured value "S" of the spherical degree of the eye E and a measured value "C" of the degree of astigmatism. The optical information V merely needs to include at least one measured value of parameters characterizing an ocular optical system, such as corneal curvature, refractive power and axial length. Among these parameters, the corneal curvature has the most influence on measurement by the fundus oculi observation device 1. Therefore, it is desired that the optical information V includes the measured value of the corneal curvature.

The measured values of the corneal curvature, refractive power and axial length are measured in advance by the same ophthalmological device as conventionally used. These measured values can be obtained from, for example, an electronic medical record server (not illustrated) connected to the fundus oculi observation device 1 via a communication line. The examiner may input measured values by operating an operation part 240B. Furthermore, it is also possible to input by reading measured values stored in a storage media with a drive device (not illustrated) of the arithmetic control device 200.

Furthermore, the optical information V may include information indicating whether an intraocular lens is placed on the eye E (intraocular lens information). In a case where an intraocular lens is placed thereon, information of the intraocular lens such as power or color may be recorded in the intraocular lens information.

The storage 212 functions as an example of the "storage" in the present invention. The storage 212 comprises, for example, a storage device such as a hard disk drive 204.

(Image Processor)

The image processor 230 includes a magnification calculator 231 and an analyzer 232. The magnification calculator 231 calculates the magnification of the ocular optical system of the eye E, and functions as an example of the "calculator" in the present invention.

Further, the analyzer 232 analyzes a tomographic image Gi, and functions as an example of the "analyzer" in the present invention. Objects of analysis by the analyzer 232 are the thickness of a layer of the fundus oculi, a defect range in a layer, the size and location of a tumor, and so on. In general, the object of analysis is any characteristic site of a fundus oculi that may be evaluated in size and location. This characteristic site is expressed, for example, in a dimension such as mm, mm2, mm3, μm, μm2, μm3. The analyzer 232 is provided with an accumulated image forming part 233, a position matching part 234, a measurement-position setting part 235, and a layer-thickness measuring part 236.

(Magnification Calculator)

The magnification calculator 231 calculates the magnification of the ocular optical system of the eye E, based on the optical information V stored in the storage 212. As described above, the optical information V is a record of measured values of corneal curvature, refractive power, axial length of the eye E and intraocular lens information. Below, an example of processes executed by the magnification calculator 231 will be described. In this embodiment, a photographing magnification is obtained in consideration of both the magnification of the eye E and the magnification of the imaging optical system 120.

First, in a case where a refractive power is a measured value at the corneal vertex (corneal refractive power), the magnification calculator 231 converts it to a refractive power at the pupil (pupil refractive power), if necessary. This calculation can be executed based on, for example, a spectacle wearing distance and a distance from the corneal vertex to the entrance pupil, as conventional.

Next, the magnification calculator 231 calculates the image forming position of a fundus oculi image by an objective lens 113. This calculation can be executed based on, for example, a pupil refractive power, a focal length of the objective lens 113, and a distance from the entrance pupil to the front focus of the objective lens 113, by using the Newton equation.

Next, the magnification calculator 231 calculates the photographing magnification of a variable magnifying lens (focusing lens) 124. This calculation can be execute by, for example, solving a quadratic equation representing a relation of the calculation result of the image forming position by the objective lens 113, and the focal length, principal focal length and overall distance of the variable magnifying lens 124, for the photographing magnification.

Next, the magnification calculator 231 calculates an angle of emission from the objective lens 113. This calculation can be executed based on, for example, the result of calculation of the photographing magnification, the distance from the rear principal point of the objective lens 113 to the imaging diaphragm 121, and the focal length of the objective lens 113. At this moment, the magnification calculator 231 calculates an emission angle so that the height of an image on the detected surface of the image becomes a predetermined value. This predetermined value is set to, for example, −0.1 mm (the minus sign indicates that the image is formed in the downward direction (−y direction) from the optical axis).

Next, the magnification calculator 231 calculates an angle of incidence to the objective lens 113 so that the height of an image on the diaphragm plane of the imaging diaphragm 121 becomes the predetermined value described above. This calculation can be performed based on, for example, the calculation result of the emission angle from the objective lens 113, and the angular magnification of the entrance pupil and the imaging diaphragm 121.

Next, the magnification calculator 231 calculates the radius of curvature of the rear face of the cornea of the eye E. This calculation can be executed based on, for example, the measured value of the corneal curvature (curvature of the front face of a cornea) recorded in the optical information V, and the proportion of the curvature of the front face and the rear face of the cornea. As the proportion of the curvature, it is possible to use a standard value based on, for example, clinical data, an eye model, or the like. For example, in the case of measuring the curvature (radius of curvature) of the rear face of a cornea by using an OCT device for cornea, it is possible to use the measured value as the radius of curvature of the rear face of the cornea.

Next, the magnification calculator 231 calculates the distance between a far point and an object (corneal vertex). This calculation can be executed based on, for example, the refractive power at the corneal vertex, and the spectacle wearing distance.

Next, the magnification calculator 231 calculates the distance from the rear face of the lens of the eye E to the retina face (fundus oculi Ef). This calculation can be executed, for example, by paraxial ray tracing based on the measured value and calculated value of the curvature (radius of curvature) of the cornea. At this moment, as an ocular optical constant, for example, a standard value based on clinical data, an eye model and so on can be used.

Next, the magnification calculator 231 calculates the axial length of the eye E. This calculation can be executed based on the calculation result by the paraxial ray tracing, and the distance from the corneal front face to the lens rear face. As this distance, it is possible to use, for example, a standard value based on clinical data, an eye model and so on.

Next, the magnification calculator 231 calculates an error between the result of calculation of the axial length and the result of measurement of the axial length (optical information V), and determines whether this error is within a specific acceptable range. For example, an error of a calculation result with respect to a measured value, namely, an absolute value of a quotient obtained by dividing a difference of the measured value and the calculation result by the measured value is obtained as the error. Further, the acceptable range of the error is preset as a threshold value for determining a value to use as an optical constant of the ocular optical system of the eye E.

In a case where the error of the axial length is within the acceptable range, for example, the measured value and calculation result of the curvature (radius of curvature) of the cornea, the measured value of the refractive power and the calculation result of the axial length are adopted as the optical constant of the eye E. Moreover, as the radius of curvature of the retina face (fundus oculi Ef), a half value of the calculation result of the axial length is adopted. Further, a value obtained by subtracting a standard value (a value of clinical data or of an eye model) of the distance from the cornea front face to the lens rear face, from the calculation result of the axial length is adopted as a distance from the lens rear face to the retina (fundus oculi Ef).

On the other hand, in a case where the error of the axial length is not within the acceptable range, the refractive power of the lens of the eye E is calculated by, for example, paraxial ray tracing using the measured values of the vertex refractive power and the axial length. Then, as an optical constant of the eye E, for example, the measured value and the calculation result of the curvature (radius of curvature) of the cornea, the measured value of the refractive power and the measured value of the axial length are adopted. Moreover, a half value of the measured value of the axial length is adopted as the radius of curvature of the retina face (fundus oculi Ef). Further, a value obtained by subtracting a standard value (value of clinical data or of an eye model) of the distance from the cornea front face to the lens rear face, from the measured value of the axial length, is adopted as the distance from the lens rear face to the retina (fundus oculi Ef).

When the optical constant of the eye E is determined, the magnification calculator 231 calculates the height of an image on the retina face (fundus oculi Ef). This calculation can be executed by, for example, ray tracing using the determined optical constant and the calculation result of the incident angle to the objective lens 113.

Finally, the magnification calculator 231 calculates the magnification, based on the calculation result of the height of the image on the retina face, the calculation result of the height of the image on the detected face, the relay magnification of a relay lens 126 (influence of the imaging optical system 120 and so on), etc. This magnification is obtained in consideration of the magnification of the ocular optical system of the eye E and the magnification of the imaging optical system 120.

Above, the calculation of a magnification in a case where an intraocular lens is not placed on the eye E has been described. In a case where an intraocular lens is placed on the eye E, the magnification calculator 231 obtains a magnification by executing the same calculation as described above using information such as the power of the intraocular lens. Here, it is determined based on the intraocular lens information, whether an intraocular lens is placed or not.

Further, in a case where a correction lens is used, the magnification calculator 231 executes calculation of the magnification of the correction lens and, in consideration of the result of this calculation, executes the same calculation as described above, thereby obtaining a targeted magnification. Here, the magnification of the corrective lens can be calculated based on the focal length of the correction lens, the distance between a focal point on the objective lens 113 side and a principal point on the object side of the corrective lens side, and the like.

(Accumulated Image Generator)

The accumulated image generator 233 generates an image (accumulated image) acquired by accumulating tomographic images Gi in the depth-wise direction (z-direction). The accumulated image generator 233 accumulates, in the depth-wise direction, depth-wise images Gij composing a tomographic image Gi, and thereby forms a dotted image at the position of each of the scanning lines Ri. The accumulated image is formed by arranging these dotted images.

Here, "accumulating in the depth-wise direction" refers to an arithmetic process of summing the luminance values (pixel values) at the depth-wise positions of the respective depth-wise images Gij. Therefore, a dotted image acquired by accumulating the depth-wise images Gij has a luminance value obtained by summing the luminance values at the z positions of the respective depth-wise images Gij.

For the respective m number of tomographic images G1-Gm, the accumulated image generator 233 accumulates the depth-wise images Gij forming the images in the depth-wise direction, and thereby forms an accumulated image composed of m×n number of dotted images that are 2-dimensionally distributed in a scanning region R of the signal light LS in acquisition of the m number of tomographic images G1-Gm.

An accumulated image is a 2-dimensional image showing the state of the surface of the fundus oculi Ef, like the fundus oculi image Ef' in the scanning region R. In general, a region photographable by a retinal camera is wider than a region photographable by an OCT device. The fundus oculi observation device 1 is used by setting the scanning region R within a photographic region of the fundus oculi image Ef'. Therefore, a region acquired as an accumulated image corresponds to part of a photographic region of the fundus oculi image Ef'. Here, it is enough as far as the photographic region of the fundus oculi image Ef' and the scanning region R are overlapped partly at least.

(Position Matching Part)

The position matching part 234 performs position matching of the fundus oculi image Ef' and an accumulated image. As described above, the accumulated image is equivalent to a partial region of the fundus oculi image Ef'. The position matching part 234 performs position matching of the both by specifying the position of the accumulated image within the fundus oculi image Ef'. In a case where part of the fundus oculi image Ef' and part of the scanning region R are overlapped, the position matching part 234 performs position matching of the overlapped regions.

The process executed by the position matching part 234 will be described more specifically. First, the position matching part 234 matches the magnification of the fundus oculi image Ef' and the magnification of the accumulated image, based on the magnification calculated by the magnification calculator 231. At this moment, the magnifications of the both are matched by changing at least one of the magnifications of the fundus oculi image Ef' and the accumulated image. By thus matching the magnifications, it is possible to shorten a processing time for the position matching.

Next, the position matching part 234 extracts characteristic points by analyzing the accumulated image. As the characteristic point, for example, a branching point of a blood vessel is extracted.

Next, the position matching part 234 analyzes the fundus oculi image Ef' and searches for the above characteristic points. At this moment, for example, the fundus oculi image Ef' (a color image) is converted to a monochrome image, and the above characteristic points are searched for in the monochrome image. This process is executed for each of the characteristic points extracted from the accumulated image.

Next, the position matching part 234 obtains coefficients of an affine transformation, based on the characteristic points within the accumulated image and the characteristic points within the fundus oculi image Ef'. A 2-dimensional affine transformation is represented by a quadratic matrix corresponding to expansion/reduction or rotation and by a constant vector corresponding to a parallel movement. The position matching part 234, for each of the characteristic points extracted from the accumulated image, substitutes a coordinate value in the accumulated image and a coordinate value in the fundus oculi image Ef', thereby determining the aforementioned quadratic matrix and constant vector. At this moment, an approximating calculation such as by the least squares method may be performed. Consequently, the coefficient of the affine transformation is determined.

The position matching part 234 applies the affine transformation to the accumulated image by using the determined coefficient, thereby matching the position of the accumulated image and the position of the fundus oculi image Ef'. Although it is also possible to transform the fundus oculi image Ef', it is desired to apply the affine transformation to the accumulated image because the accumulated image generally corresponds to part of the fundus oculi image Ef', as described above.

In the above process, position matching is conducted after the magnifications of the accumulated image and the fundus oculi image Ef' are matched. However, it is also possible to match the magnifications of the tomographic images at first, form the accumulated image, and then perform position matching.

(Measurement-Position Setting Part)

Figure 17:
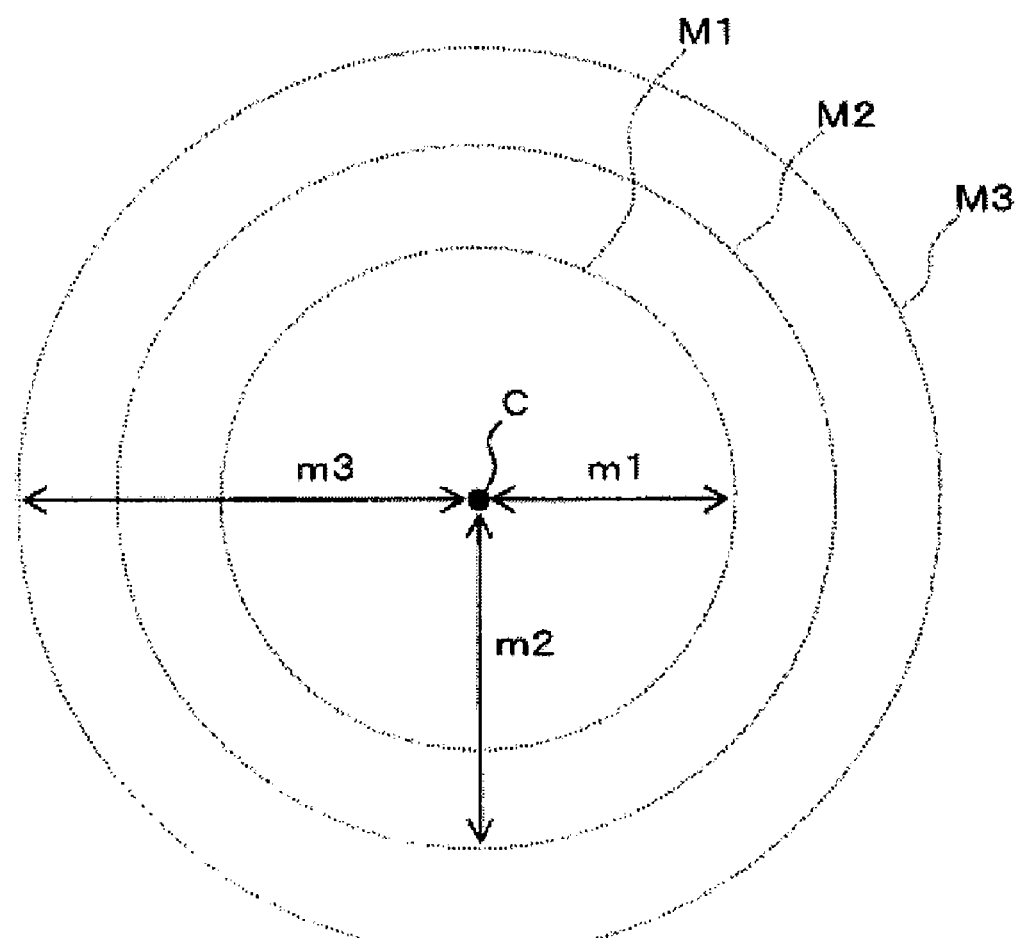
FIG. 17 is a schematic diagram showing an example of the feature of setting a measurement position for measuring the thickness of a layer of the fundus oculi.

The measurement-position setting part 235 sets the measurement positions of the fundus oculi Ef, based on the result of position matching of the accumulated image and the fundus oculi image Ef' by the position matching part 234. In this embodiment, circular measurement lines M1, M2 and M3 are set as the measurement positions as shown in FIG. 17, but it is possible to set any measurement positions in accordance with the content of measurement.

An example of a process executed by the measurement-position setting part 235 will be described. First, the measurement-position setting part 235 analyzes the fundus oculi image Ef', and specifies a position (papilla center position) within the fundus oculi image Ef' corresponding to the center of the optical papilla of the fundus oculi Ef. This process is conducted by, for example, analyzing the pixel values of the fundus oculi image Ef', extracting a region with high luminance (an image region corresponding to the optical papilla), and obtaining the position of the gravity center of the image region to set it at the papilla center position. Further, it is also possible to obtain an ellipse approximate to an image region corresponding to the optical papilla, and obtain the center (central point between two focal points) of this ellipse and set it at the papilla center position. The method for specifying the papilla center position is optional.

Next, the measurement-position setting part 235 sets the measurement lines M1, M2 and M3 on the fundus oculi image Ef'. For this, the measurement-position setting part 235 takes the specified papilla center position as a center C (ref. FIG. 17), and sets a circular region with a radius m1=1.2 mm for the measurement line M1, a circular region with a radius m2=1.6 mm for the measurement line M2, and a circular region with a radius m3=2.0 mm for the measurement line M3.

Furthermore, the measurement-position setting part 235 specifies the position in a tomographic image Gi corresponding to each of the measurement lines M1, M2 and M3 having been set on the fundus oculi image Ef'. This process is described more specifically.

The positions of the fundus oculi image Ef' and the accumulated image have been matched with each other by the position matching part 234. Therefore, the coordinate system of the fundus oculi image Ef' and the coordinate system of the accumulated image are associated with each other so as to enable coordinate conversion.

Further, the accumulated image after position matching with the fundus oculi image Ef' is an image acquired by accumulating tomographic images Gi in the depth-wise direction, and further, applying the abovementioned affine transformation. Therefore, a coordinate system to define the accumulated image and a coordinate system to define the tomographic image Gi are associated with each other so as to enable coordinate conversion.

Thus, coordinate conversion between a coordinate system to define the fundus oculi image Ef' and a coordinate system to define the tomographic image Gi is possible.

The respective measurement lines M1, M2 and M3 are set on the fundus oculi image Ef'. Therefore, the positions of the respective measurement lines M1, M2 and M3 are represented by a coordinate system to define the fundus oculi image Ef'. The measurement-position setting part 235 converts coordinate values representing the respective measurement lines M1, M2 and M3 to coordinate values of the coordinate system to define the tomographic image Gi. Consequently, the positions on the tomographic image Gi corresponding to the respective measurement lines M1, M2 and M3 are specified. The measurement-position setting part 235 sets these specified positions as measurement positions.

(Layer-Thickness Measuring Part)

The layer-thickness measuring part 236 measures the thickness of a layer of the fundus oculi Ef at the measurement positions set by the measurement-position setting part 235. A process for this measurement will be described.

First, the layer-thickness measuring part 236 obtains the position of a specific layer of the fundus oculi Ef at the measurement positions set by the measurement-position setting part 235. For this, the layer-thickness measuring part 236 executes a process as described below, for example.

The layer-thickness measuring part 236 forms a tomographic image at the set measurement positions (measurement tomographic image). This process can be executed by, for example, specifying the position of volume data corresponding to a measurement position and forming a tomographic image with the specified position as a cross section. Because the volume data is formed from a tomographic image Gi, it is possible to specify the position in the volume data corresponding to the measurement position. Instead of forming a measurement tomographic image from volume data, it is also possible to form a measurement tomographic image from tomographic images Gi.

Next, in order to make it easy to obtain the layer position of the fundus oculi Ef in the measurement tomographic image, the layer-thickness measuring part 236 executes a specific preliminary process. As this preliminary process, an optional image process is executed as necessary, such as a tone conversion process, an image enhancement process, a threshold process, a contrast conversion process, a binarization process, an edge detection process, an image averaging process, an image smoothing process and a filtering process. These image processes may be executed in combination as necessary.

Next, the layer-thickness measuring part 236 analyzes pixel values (for example, luminance values) of pixels constituting the measurement tomographic image to which the preliminary process has been applied, line by line along the depth-wise direction of the fundus oculi Ef.

That is, a measurement tomographic image is composed of a plurality of depth-wise images Gij arranged along a cross section corresponding to the measurement positions (and depth-wise images interpolating the spaces therebetween). The layer-thickness measuring part 236, for each of these depth-wise images, sequentially refers to the pixel values of pixels composing the depth-wise image, along the depth-wise direction, thereby specifying a pixel at a border position between adjacent layers. At this moment, a pixel at the border position between the layers is specified by using a filter spreading only in the depth-wise direction (for example, a differential filter).

Conventionally, in the process of specifying the position of a layer, edge detection has been applied to a tomographic image by using a filter (area filter) spreading in two directions of depth-wise direction and direction orthogonal thereto. On the other hand, in this embodiment, edge detection is executed in the depth-wise direction by using a 1-dimensional filter (line filter) spreading only in the depth-wise direction, whereby a processing time for the edge detection is shortened. Moreover, by executing this process, it is possible to execute edge detection with high accuracy. The line filter for the edge detection is previously stored in a hard disk drive 204, or the like. However, it is also possible to employ the same edge detection process as conventional.

Further, the layer-thickness measuring part 236 obtains an image region corresponding to a border position between layers of the fundus oculi Ef in a measurement tomographic image, and also, it obtains an image region corresponding to a layer of the fundus oculi Ef. That is, since the fundus oculi Ef is composed of a plurality of layers, specification of a layer is synonymous with specification of a border position between layers.

The fundus oculi Ef includes the retina, the choroidea and the sclera in this order along the depth-wise direction from the fundus oculi surface side. Further, the retina includes the inner limiting membrane, the nerve fiber layer, the ganglion cell layer, the inner plexiform layer, the internal nuclear layer, the outer plexiform layer, the outer nuclear layer, the outer limiting membrane, the photoreceptor layer and the retinal pigment epithelium layer in this order along the depth-wise direction from the fundus oculi surface side (may vary depending on sites of the fundus oculi Ef). The layer-thickness measuring part 236 also obtains the position of a layer of at least one of the above layers (namely, the boarder position between layers).

Here, it is assumed that the "layer" includes, not only the abovementioned layers composing the retina, but also the choroidea, the sclera, an organ outside thereof and so on. Further, it is assumed that the border position between layers includes, not only the border positions of the abovementioned layers composing the retina, but also the border position between the inner limiting membrane and the vitreous body, the border position between the retinal pigment epithelium layer and the choroidea, the border position between the choroidea and the sclera, the border position between the sclera and the organ outside thereof.

The layer-thickness measuring part 236 calculates the thickness of a specific site of the fundus oculi Ef, based on the position of the specific layer of the fundus oculi Ef in a measurement tomographic image. Here, it is assumed that the specific site of the fundus oculi Ef means a site of one or more layers in a plurality of aforementioned layers of the fundus oculi Ef. For example, the retinal pigment epithelium layer alone is equivalent to the "specific site," and a plurality of layers from the inner limiting membrane to the internal nuclear layer is also equivalent to the "specific site".

Further, the "specific site" subjected to the thickness calculation is, for example, the thickness from the inner limiting membrane to the nerve fiber layer (nerve fiber layer thickness), the thickness from the inner limiting membrane to the internal nuclear layer (photoreceptor inner and outer segment) (retina thickness; a first definition), the thickness from the inner limiting membrane to the retinal pigment epithelium layer (retina thickness; a second definition), or the like.

As described before, the layer-thickness measuring part 236 obtains the position (border position) of a layer of the fundus oculi Ef in a measurement tomographic image. At this moment, at least two border positions are obtained. The layer-thickness measuring part 236 obtains the thickness of a targeted layer by calculating at least two border positions among border positions have been obtained.

More specifically, the layer-thickness measuring part 236, for each of the depth-wise images composing a measurement tomographic image, calculates a distance (depth-wise distance) between pixels corresponding to the two specific border positions. To each pixel of the depth-wise image, x-y-z coordinate values are assigned (x coordinate value and y coordinate value are constant, respectively). The layer-thickness measuring part 236 is capable of calculating the distance between pixels from these coordinate values. Further, the layer-thickness measuring part 236 is also capable of calculating a targeted distance, based on the number of pixels between pixels corresponding to the two specific border positions and the distance (already known) between the adjacent pixels.

In this embodiment, circular measurement lines M1, M2 and M3 are set. Therefore, the layer-thickness measuring part 236 obtains the thickness of a layer for a measurement tomographic image corresponding to each of the measurement lines M1, M2 and M3. Each measurement tomographic image is a tomographic image having a cylindrically-shaped cross section. The layer-thickness measuring part 236 obtains the thickness of a layer, for each measurement tomographic image, at every one degree (namely, at 360 locations on a circumference), for example.

The layer-thickness measuring part 236 can also form layer-thickness graph information indicating the distribution of thickness of a layer at set measurement positions, based on the thickness of layers obtained as described above. Further, the layer-thickness measuring part 236 operates so as to summarize the obtained layer-thickness in a predetermined output format (template).

[Usage Pattern]

Figure 10:
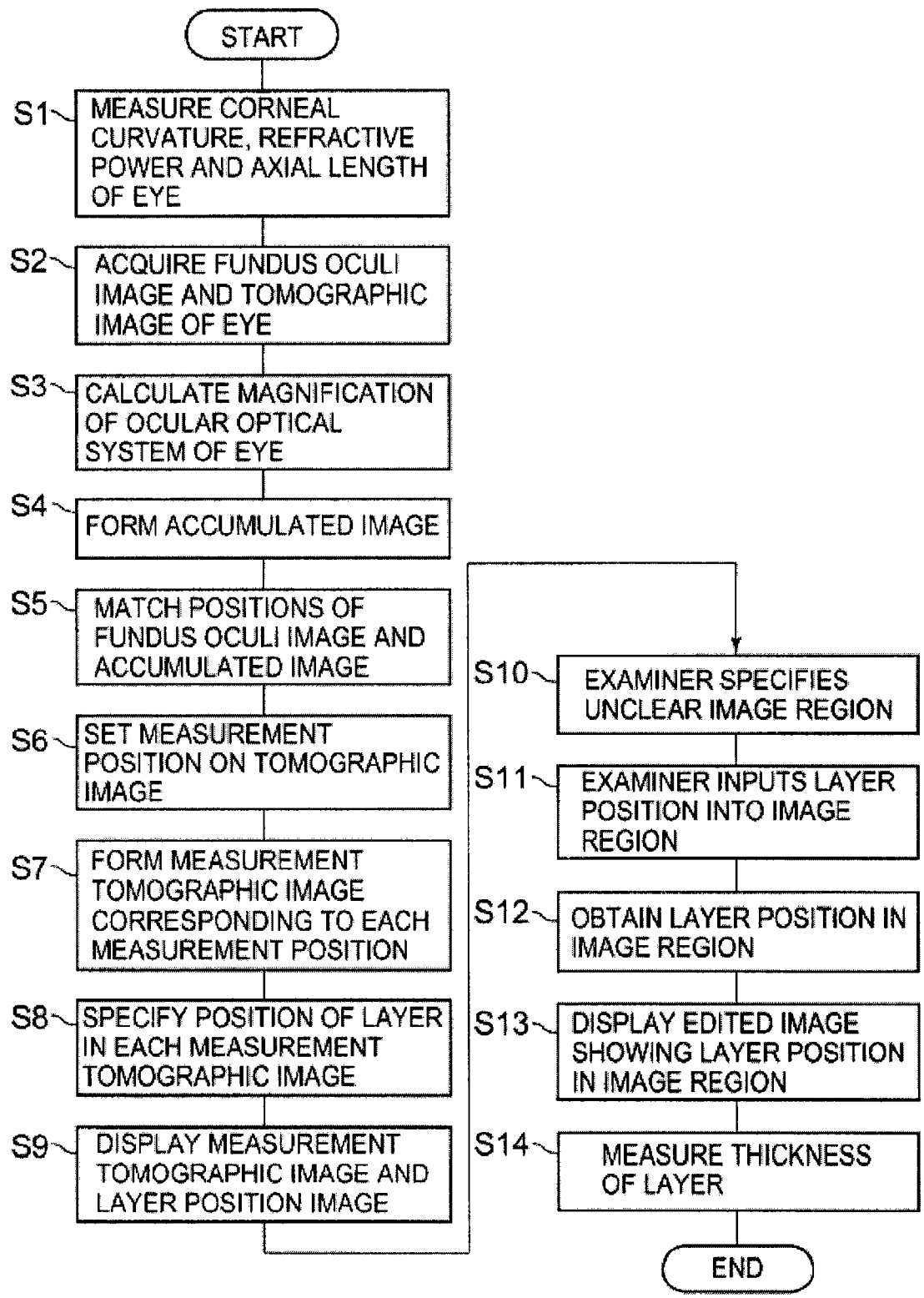
FIG. 10 is a flowchart showing an example of a usage pattern in the preferred embodiment of the fundus oculi observation device according to the present invention.

A usage pattern of the fundus oculi observation device 1 having the configuration as described above will be explained. A flowchart of FIG. 10 shows an example of the usage pattern of the fundus oculi observation device 1.

First, the corneal curvature, refractive power and axial length of the eye E are measured (S1). This measurement is conducted, for example, by using a testing device dedicated therefor. The measured values are inputted into the fundus oculi observation device 1 via a communication line or a storage medium, and stored into the storage 212 as the optical information V. Intraocular lens information is also inputted into the fundus oculi observation device 1 and stored as the optical information V.

By using the fundus oculi observation device 1, the Fundus oculi image Ef' and to inographic images Gi of the eye E are acquired (S2). The acquired fundus oculi image Ef' and tomographic images Gi are stored into the storage 212.

Either of measurement of the corneal curvature etc. or acquisition of images of the eye E may be conducted first. Further, there is no need to perform measurement of the corneal curvature etc. in a series of flow as in this usage pattern, and values having been measured on separate occasions in the past may be used.

When the optical information V, the fundus oculi image Ef' and the tomographic images Gi are acquired, the magnification calculator 231 calculates the magnification of the ocular optical system of the eye E, based on the optical information V (S3).

Next, the accumulated image forming part 233 forms an accumulated image by accumulating the tomographic images Gi in the depth-wise direction (S4). The position matching part 234 conducts position matching of the fundus oculi image Ef' and the accumulated image, based on the magnification having been calculated in Step 3 (S5).

Subsequently, the measurement-position setting part 235 sets, on the tomographic images Gi, measurement positions corresponding to the respective measurement lines M1, M2 and M3, based on the result of the position matching of the fundus oculi image Ef' and the accumulated image (S6). At this moment, it is also possible to, instead of setting the measurement positions on the tomographic images Gi, set the measurement positions on a 3-dimensional image (volume data) based on the tomographic images Gi.

Next, the layer-thickness measuring part 236 forms measurement tomographic images corresponding to the respective measurement lines M1, M2 and M3 (S7). Further, the layer-thickness measuring part 236 analyzes each of the measurement tomographic images, and specifies the position of a specific layer (S8).

The main controller 211 causes a display part 240A to display the measurement tomographic images having been formed in Step 7 and the layer position (border position) having been specified in Step 8 (S9). At this moment, all of the measurement tomographic images corresponding to the measurement lines M1, M2 and M3 may be displayed, or any of them may be displayed selectively.

Figure 11:
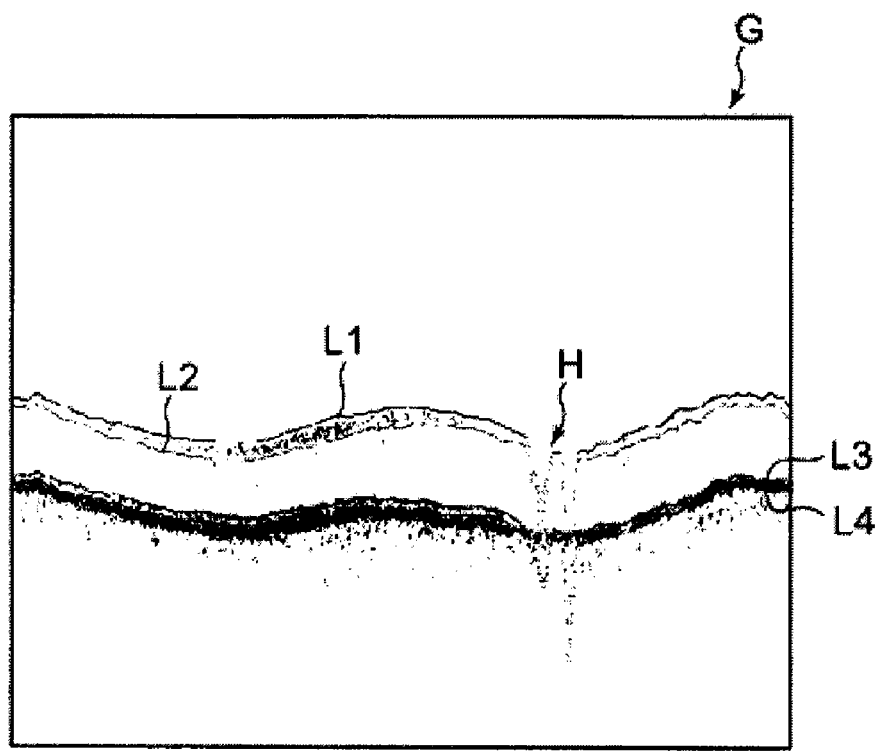
FIG. 11 is a schematic diagram showing an example of a display screen displayed in the preferred embodiment of the fundus oculi observation device according to the present invention.

FIG. 11 shows an example of a mode of displaying a measurement tomographic image and a layer position. In the display mode shown in FIG. 11, a measurement tomographic image G is displayed, and layer position images L1, L2, L3 and L4 showing the layer position (border position) having been specified by analysis of the measurement tomographic image G are also displayed.

When a measurement tomographic image is displayed, a region where fundus oculi blood vessels exist may be displayed as an unclear image due to an influence of scatter of the signal light LS caused by a blood vessel wall or blood. An image region H shown in FIG. 11 represents such an unclear image region. It is difficult to accurately detect the position of a layer in the unclear image region H. In this case, as described below, it is possible to manually edit the position of the layer while observing the measurement tomographic image G.

First, an examiner operates an operation part 240B and designates a region to be edited, namely, the unclear image region H (S10). This designating operation is conducted by, for example, dragging a mouse 206. It is also possible to erase an image within the designated image region H.

Figure 12:
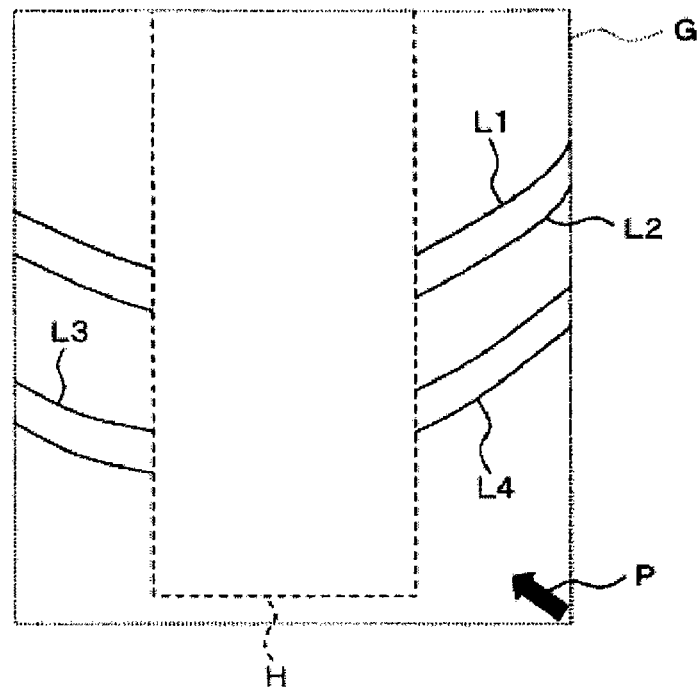
FIG. 12 is a schematic diagram showing an example of a display screen displayed in the preferred embodiment of the fundus oculi observation device according to the present invention.

FIG. 12 shows a magnified image of the designated image region H and the periphery thereof. The examiner observes the measurement tomographic image G to grasp the position of a layer in the image region H. Then, the examiner operates the operation part 240B and inputs the grasped layer position on the image region H (S11). This operation is conducted by, for example, an operation of clicking the mouse 206. Symbol P in FIG. 12 denotes a mouse pointer.

Figure 13:
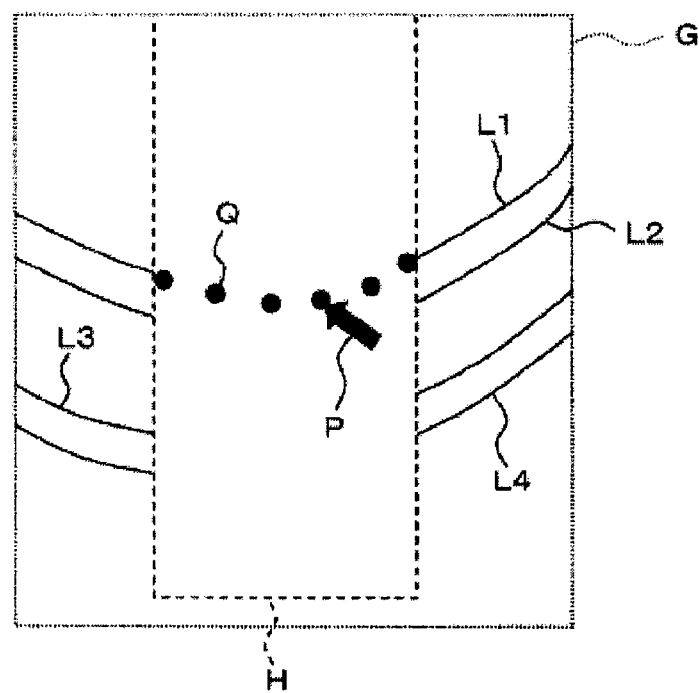
FIG. 13 is a schematic diagram showing an example of a display screen displayed in the preferred embodiment of the fundus oculi observation device according to the present invention.

FIG. 13 shows an example of a method of inputting the layer position. The examiner operates the mouse 206, moves the mouse pointer P to the grasped layer position, and clicks. The main controller 211 controls to display a dot image Q at the position designated by the click operation. The dot image Q in FIG. 13 represents the position of a layer in the image region H corresponding to the layer position image L1.

The layer-thickness measuring part 236 obtains the position of a layer in the image region H, based on the layer position having been inputted by the examiner (S12). As an example, in a case where the dot images Q are designated, the layer-thickness measuring part 236 obtains lines (spline curves etc.) passing through the respective dot images Q. Further, it is also possible to obtain an optional approximating curve (for example, Bezier curve) acquired from the positions of the respective dot images Q. Moreover, it is desirable to obtain the position of a layer in the image region H so as to be smoothly connected to the layer position image L1, by referring to not only the dot images Q but also the state (inclination etc.) of the layer position image L1 etc. near the image region H.

Figure 14:
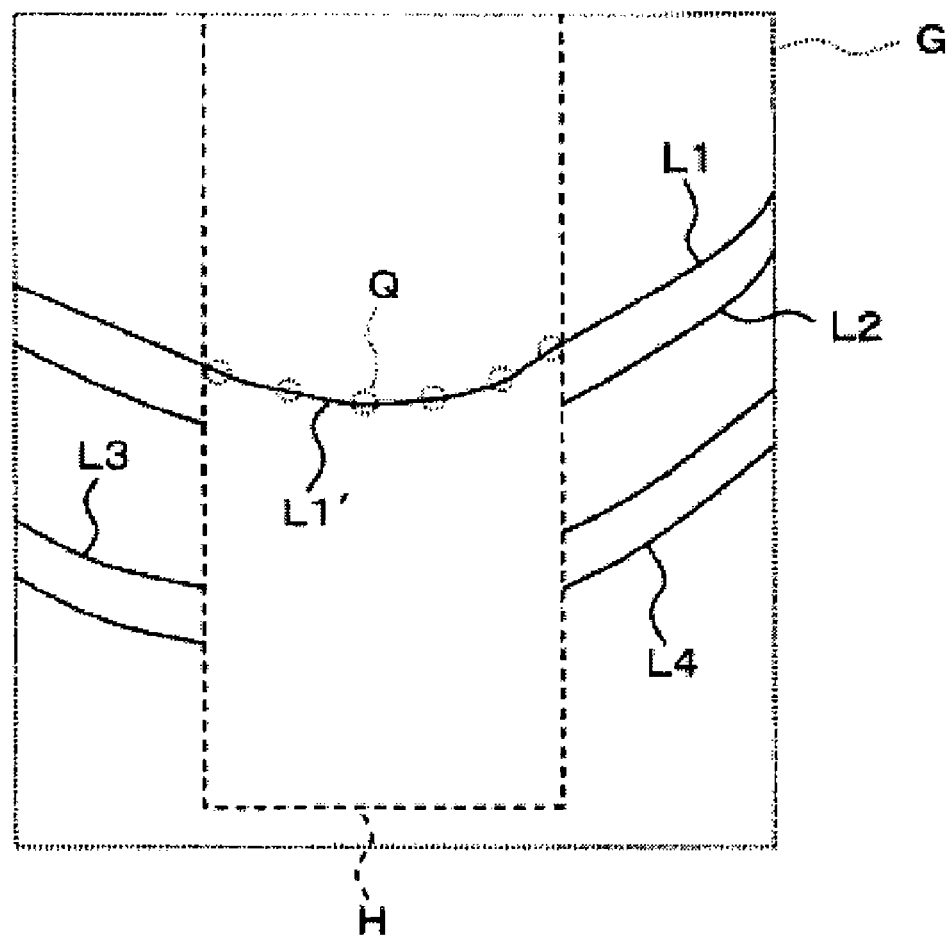
FIG. 14 is a schematic diagram showing an example of a display screen displayed in the preferred embodiment of the fundus oculi observation device according to the present invention.

The main controller 211 controls to display an image (edited image) showing the obtained layer position within the image region H (S13). FIG. 14 shows a mode of displaying an edited image L1' based on the dot images Q in FIG. 13. The processes of Steps 10-13 are described in detail in Japanese Patent Application No. 2006-252953 by the present applicant. It is also possible not to perform the abovementioned edition of the position of a layer. In this case, it is desirable not to measure the thickness of a layer in the unclear image region H. This is for prevention of obtaining inappropriate measurement results. When the layer position is specified, the layer-thickness measuring part 236 measures the thickness of a specific layer, based on the specified layer position. Moreover, the layer-thickness measuring part 236 summarizes the result of measurement of thickness of layers in a predetermined output format. In this output format, for example, for each of three measurement tomographic images, the result of measurement in each of the upward direction, the downward direction, the direction toward the nose and the direction toward the ear is summarized in table format. In this measurement result, information on the eye E such as the optical information V, and information on a examined person (patient ID, patient name, etc.) are also recorded. The measurement result is printed out by a printer (not illustrated), or sent to a server or the like via a communication line.

[Actions and Advantageous Effects]

The actions and advantageous effects of the fundus oculi observation device 1 as described above will be described.

The fundus oculi observation device 1 is an OCT device that detects the interference light LC based on the low-coherence light L0 and, based on the detection result, forms the tomographic images Gi of the fundus oculi Ef. The formed tomographic images Gi are stored into the storage 212 together with the optical information V indicating the state of the ocular optical system of the eye E. The magnification calculator 231 calculates the magnification of the ocular optical system of the eye E, based on the optical information V. The analyzer 232 analyzes the tomographic images Gi, based on this magnification. To be specific, in this embodiment, the thickness of a layer of the fundus oculi Ef is obtained by analyzing the tomographic images Gi.

According to the fundus oculi observation device 1 that acts in this way, it is possible to calculate a magnification based on the optical information V indicating the state of the ocular optical system of the eye E. In particular, there is no need to execute a conventional estimating process using refractive power of the Gullstrand's eye model. Therefore, according to the fundus oculi observation device 1, it is possible to accurately obtain a magnification in accordance with the eye E.

Further, in a case where an intraocular lens is placed onto the eye E, the fundus oculi observation device 1 acts so as to calculate a magnification, based on information such as the power of the intraocular lens. Therefore, it is possible to accurately obtain a magnification even if an intraocular lens is placed on the eye E.

Further, the fundus oculi observation device 1 has, not only a function of forming the tomographic images Gi, but also a function of capturing a 2-dimensional image of the surface of the fundus oculi Ef (fundus oculi image Ef'). The captured fundus oculi image Ef' is stored into the storage 212. The analyzer 232 accumulates the tomographic images Gi in the depth-wise direction of the fundus oculi Ef, and forms an accumulated image. Furthermore, the analyzer 232 conducts position matching of the fundus oculi image Ef' and the accumulated image based on the highly accurate magnification having been obtained by the magnification calculator 231. Therefore, according to the fundus oculi observation device 1, it is possible to accurately perform position matching of the fundus oculi image Ef' and the accumulated image. Consequently, it is possible to accurately perform position matching between the fundus oculi image Ef' and the tomographic images Gi (and the 3-dimensional image of the fundus oculi Ef), and hence it becomes possible to accurately associate positions on the fundus oculi image Ef' with positions on the tomographic image Gi.

Moreover, the analyzer 232 acts so as to set a measurement position of the fundus oculi Ef, based on the result of position matching between the fundus oculi image Ef' and the accumulated image and obtain the thickness of a layer of the fundus oculi Ef at the measurement position, based on the tomographic image Gi (or 3-dimensional image). According to the fundus oculi observation device 1, it is possible to accurately associate positions on the fundus oculi image Ef' with positions on the tomographic image Gi as described above, so that it is possible to accurately set a measurement position on the tomographic image Gi. Therefore, according to the fundus oculi observation device 1, it is possible to reduce errors in measurement due to displacement between the fundus oculi image Ef' and the tomographic image Gi.

[Modification]

The configuration described in detail above is merely an example for implementing the fundus oculi observation device related to the present invention. Therefore, any modification may be applied within the scope of the present invention as necessary.

In the above embodiment, the result of position matching between the fundus oculi image Ef' and the accumulated image is used for measurement of the thickness of a layer of the fundus oculi, but the usage is not limited thereto. For example, it is possible to, by using the result of position matching, increase the accuracy of scan of the signal light LS. A concrete example will be described below.

The scanning region R is usually set referring to the fundus oculi image Ef'. However, due to an influence of the ocular optical system of the eye E, a position on the fundus oculi image Ef' may be displaced from the scan position of the signal light LS. If such displacement is caused, a tomographic image at a position different from the position (cross section) having been set based on the fundus oculi image Ef' is acquired, and reexamination is required. Moreover, it is particularly difficult for an examiner who is not well trained in examinations to set cross-sections on the fundus oculi image Ef' while considering the displacement.

Therefore, in this modification, these problems will be solved by conducting the following processes. First, a cross-section is set by capturing the fundus oculi image Ef', and the tomographic images Gi are acquired. Next, an accumulated image is formed based on the tomographic images Gi, and position matching with the fundus oculi image Ef' is performed.

The analyzer 232 sets scan positions in the fundus oculi Ef, based on the result of the position matching. This process can be conducted by associating the scan positions set on the fundus oculi image Ef' with the position on the accumulated image (tomographic image Gi), based on the previously described coordinate conversion in the position matching process.

The main controller 211 controls the mirror driving mechanisms 241 and 242 (ref. FIG. 5) so as to scan the set scan positions with the signal light LS. In this way, a tomographic image at a desired cross-section on the fundus oculi image Ef' may be acquired.

Although the fundus oculi observation device 1 in the above embodiment is a Fourier Domain type OCT device, the configuration of the present invention may be applied to an OCT device of an optional type, such as Time Domain type, Full Field type, Swept Source type, or the like.

[Fundus Oculi Image Processing Device]

A fundus oculi image processing device related to the present invention will be described.

A fundus oculi image processing device comprises, for example, a computer connected with a retinal camera and an OCT device so as to be communicable. Further, the fundus oculi image processing device comprises a computer capable of receiving images acquired by the retinal camera and the OCT device via storage media. This computer is provided with a microprocessor, a RAM, a ROM, a hard disk drive, and so on (ref. FIG. 4). Moreover, this computer can be configured in the same manner as the arithmetic control device 200 shown in FIG. 7.

The fundus oculi image processing device comprises a computer including a storage, a calculator, and an analyzer. The storage stores tomographic images of a fundus oculi of an eye and optical information indicating the state of the ocular optical system of the eye. The calculator calculates the magnification of the ocular optical system of the eye E, based on the optical information stored in the storage. The analyzer analyzes the tomographic images stored in the storage, based on the calculated magnification.

In the aforementioned arithmetic control device 200, the storage 212 is an example of the storage, the magnification calculator 231 is an example of the calculator, and the analyzer 232 is an example of the analyzer.

According to such a fundus oculi image processing device, it is possible to calculate a magnification, based on the optical information indicating the state of the ocular optical system of the eye, and there is no need to perform a conventional estimating process using the refractive power of the Gullstrand's eye model, so that it is possible to accurately obtain a magnification in accordance with the eye.

Further, it is possible to apply a fundus oculi image processing device configured in the same manner as the arithmetic control device 200 in the above embodiment. Consequently, the fundus oculi image processing device can apply processes, as in the arithmetic control device 200, to an eye onto which an intraocular lens is placed. Moreover, the fundus oculi image processing device can also conduct a process of forming an accumulated image, and a process of position matching between a fundus oculi image and an accumulated image. Furthermore, the fundus oculi image processing device can also conduct a process of setting measurement positions, and a process of measuring the thickness of a layer of the fundus oculi.

According to the present invention, it is possible to calculate the magnification of the ocular optical system based on optical information that indicates the state of the ocular optical system of an eye, and analyze tomographic images of the eye based on the calculated magnification. This eliminates the need for an arithmetic process based on information other than information proprietary to the eye. For example, there is no need to estimate the corneal curvature of an eye by using the refractive power of the Gullstrand's eye model as conventional. Therefore, it is possible to accurately obtain the magnification of the ocular optical system for each eye.

What is claimed is:

1. A fundus oculi observation device comprising:
    an image forming part configured to optically acquire data by imaging through an imaging optical system and form a tomographic image of a fundus oculi of an eye;
    a storage configured to store optical information representing a state of an ocular optical system of the eye, the optical information including at least one of measured values of corneal curvature, refractive power and axial length of the eye;
    a calculator configured to calculate a magnification of the ocular optical system, based on the optical information, wherein the calculator is configured to calculate a magnification of the imaging optical system;
    a measurement position setting part configured to specify and set measurement positions of the fundus oculi; and
    an analyzer configured to analyze the tomographic image, in order to determine a thickness of a layer of the fundus oculi at the measurement positions set by the measurement position setting part, based on the magnification of the ocular optical system and the magnification of the imaging optical system.

2. The fundus oculi observation device according to claim 1, wherein:
    the optical information includes intraocular lens information representing whether an intraocular lens is placed on the eye; and
    the calculator determines whether the intraocular lens exists based on the intraocular lens information and, when determining that the intraocular lens exists, calculates the magnification based on a refractive power of the intraocular lens placed on the eye, instead of the measured value of the refractive power.

3. The fundus oculi observation device according to claim 1, wherein:
    the image forming part captures a 2-dimensional image of a surface of the fundus oculi; and
    the analyzer accumulates the tomographic images in a depth-wise direction of the fundus oculi to form an accumulated image, and executes position matching of the 2-dimensional image and the accumulated image based on the magnification.

4. The fundus oculi observation device according to claim 3, wherein:
the analyzer sets a measurement position of the fundus oculi based on a result of the position matching, and obtains thickness of a layer of the fundus oculi at the measurement position, based on the tomographic image.

5. The fundus oculi observation device according to claim 4, wherein:
the analyzer specifies a position in the 2-dimensional image corresponding to a center of the optical papilla, and sets a circular region having a specific radius about the specified position, as the measurement position.

6. The fundus oculi observation device according to claim 3, wherein:
the analyzer sets a scan position on the fundus oculi, based on a result of the position matching; and
the image forming part acquires new data by optically scanning the fundus oculi based on the set scan position, and forms a new tomographic image of the fundus oculi based on the acquired new data.

7. A fundus oculi image processing device comprising:
a storage configured to store tomographic images of a fundus oculi of an eye obtained through an imaging optical system and optical information indicating a state of an ocular optical system of the eye, the optical information including at least one of measured values of corneal curvature, refractive power and axial length of the eye; and
a calculator configured to calculate a magnification of the ocular optical system, based on the optical information, wherein the calculator is configured to calculate a magnification of the imaging optical system;
a measurement position setting part configured to specify a layer included in the fundus oculi; and
an analyzer configured to analyze the tomographic images, in order to determine a thickness of a layer of the fundus oculi at the measurement positions set by the measurement position setting part, based on the magnification of the ocular optical system and the magnification of the imaging optical system.

8. The fundus oculi image processing device according to claim 7, wherein:
the optical information includes intraocular lens information indicating whether an intraocular lens is placed on the eye; and
the calculator determines whether the intraocular lens exists based on the intraocular lens information and, when determining that the intraocular lens exists, calculates the magnification based on a refractive power of the intraocular lens placed on the eye, instead of the measured value of the refractive power.

9. The fundus oculi image processing device according to claim 7, wherein:
the storage stores a 2-dimensional image of a surface of the fundus oculi; and
the analyzer accumulates the tomographic images in a depth-wise direction of the fundus oculi to form an accumulated image, and executes position matching of the 2-dimensional image and the accumulated image, based on the magnification.

10. The fundus oculi image processing device according to claim 9, wherein:
the analyzer sets measurement positions of the fundus oculi based on a result of the position matching, and obtains the thickness of a layer of the fundus oculi at the measurement positions, based on the tomographic images.

11. The fundus oculi image processing device according to claim 10, wherein:
the analyzer specifies a position in the 2-dimensional image corresponding to the center of the optical papilla, and sets a circular region having a specific radius about the specified position, as the measurement position.

12. The fundus oculi observation device according to claim 1, wherein:
the magnification of the imaging optical system is a photographing magnification of a variable magnifying lens.

13. The fundus oculi observation device according to claim 7, wherein:
the magnification of the imaging optical system is a photographing magnification of a variable magnifying lens.

* * * * *